United States Patent
Ackermann et al.

(10) Patent No.: US 10,143,846 B2
(45) Date of Patent: Dec. 4, 2018

(54) SYSTEMS AND METHODS FOR TREATMENT OF DRY EYE

(71) Applicant: The Board of Trustees of the Leland Stanford Junior University, Stanford, CA (US)

(72) Inventors: Douglas Michael Ackermann, San Francisco, CA (US); Daniel Palanker, Palo Alto, CA (US); James Donald Loudin, Houston, TX (US); Garrett Cale Smith, San Francisco, CA (US); Victor Wayne McCray, San Jose, CA (US); Brandon McNary Felkins, Half Moon Bay, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/828,950

(22) Filed: Dec. 1, 2017

(65) Prior Publication Data
US 2018/0154161 A1 Jun. 7, 2018

Related U.S. Application Data

(63) Continuation of application No. 14/816,846, filed on Aug. 3, 2015, which is a continuation of application
(Continued)

(51) Int. Cl.
*A61N 1/37* (2006.01)
*A61N 1/372* (2006.01)
(Continued)

(52) U.S. Cl.
CPC ....... *A61N 1/37205* (2013.01); *A61N 1/3606* (2013.01); *A61N 1/36046* (2013.01);
(Continued)

(58) Field of Classification Search
CPC ......... A61F 2007/0004; A61F 9/00772; A61N 1/0546; A61N 1/36046; A61N 1/37205
See application file for complete search history.

(56) References Cited

U.S. PATENT DOCUMENTS

| | | |
|---|---|---|
| 4,520,825 A | 6/1985 | Thompson et al. |
| 4,539,988 A | 9/1985 | Shirley et al. |

(Continued)

FOREIGN PATENT DOCUMENTS

| | | |
|---|---|---|
| CN | 101939043 A | 1/2011 |
| EP | 3263175 A1 | 1/2018 |

(Continued)

OTHER PUBLICATIONS

Extended European Search Report dated Jan. 8, 2018, for EP Application No. 15824539.9, filed on Jul. 24, 2015, 6 pages.
(Continued)

*Primary Examiner* — Amanda Hulbert
(74) *Attorney, Agent, or Firm* — Shay Glenn LLP

(57) ABSTRACT

A stimulation system stimulates anatomical targets in a patient for treatment of dry eye. The system may include a controller and a microstimulator. The controller may be implemented externally to or internally within the microstimulator. The components of the controller and microstimulator may be implemented in a single unit or in separate devices. When implemented separately, the controller and microstimulator may communicate wirelessly or via a wired connection. The microstimulator may generate pulses from a controller signal and apply the signal via one or more electrodes to an anatomical target. The microstimulator may not have any intelligence or logic to shape or modify a signal. The microstimulator may be a passive device configured to generate a pulse based on a signal received from the controller. The microstimulator may shape or modify a signal. Waveforms having different frequency, amplitude
(Continued)

and period characteristics may stimulate different anatomical targets in a patient.

17 Claims, 17 Drawing Sheets

Related U.S. Application Data

No. 14/561,107, filed on Dec. 4, 2014, now Pat. No. 9,095,723, which is a continuation of application No. 13/298,042, filed on Nov. 16, 2011, now Pat. No. 8,918,181.

(60) Provisional application No. 61/414,293, filed on Nov. 16, 2010, provisional application No. 61/433,645, filed on Jan. 18, 2011, provisional application No. 61/433,649, filed on Jan. 18, 2011, provisional application No. 61/433,652, filed on Jan. 18, 2011.

(51) Int. Cl.
*A61N 1/36* (2006.01)
*A61N 1/375* (2006.01)
*A61N 1/378* (2006.01)

(52) U.S. Cl.
CPC ....... *A61N 1/36142* (2013.01); *A61N 1/3756* (2013.01); *A61N 1/3787* (2013.01); *A61N 1/36057* (2013.01); *A61N 1/37211* (2013.01)

(56) References Cited

U.S. PATENT DOCUMENTS

| | | | |
|---|---|---|---|
| 4,628,933 A | 12/1986 | Michelson |
| 4,868,154 A | 9/1989 | Gilbard et al. |
| 5,025,807 A | 6/1991 | Zabara |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,345,948 A | 9/1994 | O'Donnell, Jr. |
| 5,360,438 A | 11/1994 | Fisher |
| 5,545,617 A | 8/1996 | Dartt et al. |
| 5,607,461 A | 3/1997 | Lathrop |
| 5,611,970 A | 3/1997 | Apollonio et al. |
| 5,697,957 A | 12/1997 | Noren et al. |
| 5,707,400 A | 1/1998 | Terry et al. |
| 5,843,140 A | 12/1998 | Strojnik |
| 5,935,155 A | 8/1999 | Humayun et al. |
| 5,948,006 A | 9/1999 | Mann |
| 6,001,088 A | 12/1999 | Roberts et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,152,916 A | 11/2000 | Bige |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,272,382 B1 | 8/2001 | Faltys et al. |
| 6,275,737 B1 | 8/2001 | Mann |
| 6,277,855 B1 | 8/2001 | Yerxa |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,535,766 B1 | 3/2003 | Thompson et al. |
| 6,539,253 B2 | 3/2003 | Thompson et al. |
| 6,564,102 B1 | 5/2003 | Boveja |
| 6,658,301 B2 | 12/2003 | Loeb et al. |
| 6,662,052 B1 | 12/2003 | Sarwal et al. |
| 6,701,189 B2 | 3/2004 | Fang et al. |
| 6,792,314 B2 | 9/2004 | Byers et al. |
| 6,829,508 B2 | 12/2004 | Schulman et al. |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,317,947 B2 | 1/2008 | Wahlstrand et al. |
| 7,330,762 B2 | 2/2008 | Boveja et al. |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,879,079 B2 | 2/2011 | Tu et al. |
| D638,128 S | 5/2011 | Prokop et al. |
| 7,981,095 B2 | 7/2011 | Grenon et al. |
| 7,998,202 B2 | 8/2011 | Lesh |
| 8,019,419 B1 | 9/2011 | Panescu et al. |
| 8,019,441 B2 | 9/2011 | Wallace et al. |
| 8,145,322 B1 | 3/2012 | Yao et al. |
| 8,204,591 B2 | 6/2012 | Ben-David et al. |
| 8,318,070 B2 | 11/2012 | Shiah et al. |
| 8,489,189 B2 | 7/2013 | Tronnes |
| 8,918,181 B2 | 12/2014 | Ackermann et al. |
| 9,079,042 B2 | 7/2015 | Tiedtke et al. |
| 9,095,723 B2 | 8/2015 | Ackermann et al. |
| 9,821,159 B2 | 11/2017 | Ackermann et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0192784 A1 | 10/2003 | Zhou |
| 2003/0233135 A1* | 12/2003 | Yee ............ A61N 1/36014 607/48 |
| 2004/0059466 A1 | 3/2004 | Block et al. |
| 2004/0098067 A1 | 5/2004 | Ohta et al. |
| 2004/0147973 A1 | 7/2004 | Hauser |
| 2004/0220644 A1 | 11/2004 | Shalev et al. |
| 2005/0004621 A1 | 1/2005 | Boveja et al. |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0105046 A1 | 5/2005 | Tung |

(56) References Cited

U.S. PATENT DOCUMENTS

| | | |
|---|---|---|
| 2005/0197675 A1 | 9/2005 | David et al. |
| 2005/0251061 A1 | 11/2005 | Schuler et al. |
| 2005/0267542 A1 | 12/2005 | David et al. |
| 2006/0004423 A1 | 1/2006 | Boveja et al. |
| 2006/0074450 A1 | 4/2006 | Boveja et al. |
| 2006/0095077 A1 | 5/2006 | Tronnes |
| 2006/0095108 A1 | 5/2006 | Chowdhury et al. |
| 2006/0100668 A1 | 5/2006 | Ben-David et al. |
| 2006/0142822 A1 | 6/2006 | Tulgar |
| 2006/0161225 A1 | 7/2006 | Sormann et al. |
| 2006/0206155 A1 | 9/2006 | Ben-David et al. |
| 2006/0235430 A1 | 10/2006 | Le et al. |
| 2006/0239482 A1 | 10/2006 | Hatoum |
| 2006/0259098 A1 | 11/2006 | Erickson |
| 2006/0271108 A1 | 11/2006 | Libbus et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0250119 A1 | 10/2007 | Tyler et al. |
| 2007/0250135 A1 | 10/2007 | Bartz-Schmidt et al. |
| 2007/0255333 A1 | 11/2007 | Giftakis et al. |
| 2007/0276314 A1 | 11/2007 | Becker |
| 2007/0299462 A1 | 12/2007 | Becker |
| 2008/0021515 A1 | 1/2008 | Horsager et al. |
| 2008/0082131 A1 | 4/2008 | Llanos |
| 2008/0109054 A1 | 5/2008 | Hastings et al. |
| 2008/0114424 A1* | 5/2008 | Grenon .............. A61F 7/12 607/96 |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0208335 A1 | 8/2008 | Blum et al. |
| 2008/0221642 A1 | 9/2008 | Humayun et al. |
| 2008/0288036 A1 | 11/2008 | Greenberg et al. |
| 2008/0294066 A1 | 11/2008 | Hetling et al. |
| 2009/0005835 A1 | 1/2009 | Greenberg et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0099626 A1 | 4/2009 | De Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0157142 A1 | 6/2009 | Cauller |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0306738 A1 | 12/2009 | Weiss et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0139002 A1 | 6/2010 | Walker et al. |
| 2010/0161004 A1 | 6/2010 | Najafi |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0274313 A1 | 10/2010 | Boling et al. |
| 2010/0280509 A1 | 11/2010 | Muller et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan et al. |
| 2011/0077698 A1 | 3/2011 | Tsampazis et al. |
| 2011/0093043 A1 | 4/2011 | Torgerson et al. |
| 2011/0152969 A1 | 6/2011 | Zehnder et al. |
| 2011/0202121 A1 | 8/2011 | Wen |
| 2011/0276107 A1 | 11/2011 | Simon et al. |
| 2011/0295336 A1 | 12/2011 | Sharma et al. |
| 2012/0197338 A1 | 8/2012 | Su et al. |
| 2012/0232615 A1 | 9/2012 | Barolat et al. |
| 2012/0253249 A1 | 10/2012 | Wilson |
| 2012/0298105 A1 | 11/2012 | Osorio |
| 2012/0323227 A1 | 12/2012 | Wolf et al. |
| 2012/0330376 A1 | 12/2012 | Flynn et al. |
| 2013/0006095 A1 | 1/2013 | Jenkins et al. |
| 2013/0178937 A1 | 7/2013 | Vassallo et al. |
| 2015/0335900 A1 | 11/2015 | Ackermann et al. |
| 2018/0064940 A1 | 3/2018 | Ackermann et al. |
| 2018/0064941 A1 | 3/2018 | Ackermann et al. |

FOREIGN PATENT DOCUMENTS

| | | | |
|---|---|---|---|
| JP | 2002519138 | A | 7/2002 |
| JP | 2002325851 | A | 11/2002 |
| JP | 2002539859 | A | 11/2002 |
| JP | 2004526510 | A | 9/2004 |
| JP | 200552461 | A | 3/2005 |
| JP | 2005521489 | A | 7/2005 |
| JP | 2006515900 | A | 6/2006 |
| JP | 200744323 | A | 2/2007 |
| JP | 2007528751 | A | 10/2007 |
| JP | 2008183248 | A | 8/2008 |
| JP | 2008541850 | A | 11/2008 |
| JP | 2010505563 | A | 2/2010 |
| JP | 201051562 | A | 3/2010 |
| JP | 2010506654 | A | 3/2010 |
| JP | 2010537777 | A | 12/2010 |
| JP | 2011030734 | A | 2/2011 |
| WO | WO00/62672 | A1 | 10/2000 |
| WO | WO2004/026106 | A2 | 4/2004 |
| WO | WO2004/091453 | A1 | 10/2004 |
| WO | WO2004/112893 | A2 | 12/2004 |
| WO | WO2004/112893 | A3 | 12/2004 |
| WO | WO 2005/060984 | A1 | 7/2005 |
| WO | WO2008/156501 | A2 | 12/2008 |
| WO | WO2009/070709 | A1 | 6/2009 |
| WO | WO2010/003011 | A1 | 1/2010 |
| WO | WO2010/069317 | A1 | 6/2010 |
| WO | WO2010/123704 | A2 | 10/2010 |
| WO | WO2010/027743 | A1 | 11/2010 |
| WO | WO 2011/011373 | A1 | 1/2011 |

OTHER PUBLICATIONS

Extended European Search Report dated Nov. 27, 2017, for EP Application No. 17167504.4, filed on Apr. 6, 2012, 9 pages.

Extended European Search Report received for European Patent Application No. 11842076.9, dated Oct. 28, 2014, 5 pages.

Extended European Search Report received for European Patent Application No. 12768458.7, dated Aug. 28, 2014, 7 pages.

Final Office Action for U.S. Appl. No. 13/441,806, dated Mar. 12, 2015, 10 pages.

Final Office Action for U.S. Appl. No. 13/441,806, dated May 20, 2016, 10 pages.

Final Office Action for U.S. Appl. No. 14/816,846, dated May 11, 2016, 12 pages.

Final Office Action dated Dec. 20, 2017, for U.S. Appl. No. 14/920,852, dated Oct. 22, 2015, 18 pages.

Final Office Action dated Mar. 28, 2018, for U.S. Appl. No. 15/598,063, filed May 17, 2017, 9 pages.

Final Office Action dated May 17, 2017, for U.S. Appl. No. 13/441,806, filed Apr. 6, 2012, 5 pages.

Final Office Action dated Sep. 1, 2017, for U.S. Appl. No. 14/816,846, filed Aug. 3, 2015, 12 pages.

Final Office Action dated Sep. 23, 2016, for U.S. Appl. No. 14/809,109, filed Jul. 24, 2015, 10 pages.

Final Office Action received for U.S. Appl. No. 14/207,072, dated Jun. 22, 2016, 20 pages.

International Search Report & Written Opinion received for PCT Patent Application No. PCT/US2014/022158, dated Jul. 30, 2014, 8 pages.

(56) References Cited

OTHER PUBLICATIONS

International Search Report and Written Opinion received for PCT Application No. PCT/US2015/042130, dated Oct. 28, 2015, 5 pages.
International Search Report and Written Opinion received for PCT Patent Application No. PCT/US2014/024496, dated Aug. 22, 2014, 11 pages.
International Search Report and Written Opinion received for PCT Patent Application No. PCT/US2015/057023, dated Mar. 4, 2016, 10 pages.
International Search Report mailed on Feb. 10, 2016, for PCT Patent Application No. PCT/US2015/57021, filed on Oct. 22, 2015, 4 pages.
International Search Report received for PCT Patent Application No. PCT/US2015/57019, dated Feb. 11, 2016, 4 pages.
Non Final Office Action received for U.S. Appl. No. 13/441,806, dated Sep. 17, 2015, 11 pages.
Non Final Office Action received for U.S. Appl. No. 14/207,072, dated Dec. 9, 2015, 8 pages.
Non-Final Office Action dated Dec. 28, 2017, for U.S. Appl. No. 15/676,910, filed Aug. 14, 2017, 10 pages.
Non-Final Office Action dated Jul. 17, 2017, for U.S. Appl. No. 15/598,063, filed May 17, 2017, 9 pages.
Non-Final Office Action dated Jul. 31, 2017, for U.S. Appl. No. 14/920,852, filed Oct. 22, 2015, 18 pages.
Non-Final Office Action dated Nov. 2, 2016, for U.S. Appl. No. 13/441,806, filed Apr. 6, 2012, 11 pages.
Non-Final Office Action dated Sep. 27, 2016, for U.S. Appl. No. 14/920,847, filed Oct. 22, 2015, 13 pages.
Non-Final Office Action Received for U.S. Appl. No. 14/920,852, dated Aug. 1, 2016, 17 pages.
Non-Final Office Action received for U.S. Appl. No. 13/298,042, dated Oct. 2, 2013, 10 pages.
Non-Final Office Action received for U.S. Appl. No. 13/441,806, dated Dec. 18, 2013, 9 pages.
Non-Final Office Action received for U.S. Appl. No. 14/201,753, dated Apr. 2, 2015, 6 pages.
Non-Final Office Action received for U.S. Appl. No. 14/809,109, dated Apr. 8, 2016, 8 pages.
Non-Final Office Action received for U.S. Appl. No. 14/816,846, dated Sep. 11, 2015, 5 pages.
Non-Final Office Action Received for U.S. Appl. No. 14/920,860, dated Aug. 17, 2016, 11 pages.
Notice of Allowance dated Apr. 20, 2017, for U.S. Appl. No. 14/920,860, filed Oct. 22, 2015, 5 pages.
Notice of Allowance dated Aug. 2, 2017, for U.S. Appl. No. 13/441,806, filed Apr. 6, 2012, 5 pages.
Notice of Allowance dated May 30, 2017, for U.S. Appl. No. 14/920,847, filed Oct. 22, 2015, 5 pages.
Notice of Allowance received for U.S. Appl. No. 14/201,753, dated Dec. 15, 2015, 2 pages.
Notice of Allowance received for U.S. Appl. No. 14/201,753, dated Oct. 15, 2015, 5 pages.
Notice of Allowance received for U.S. Appl. No. 13/298,042, dated Apr. 29, 2014, 5 pages.
Notice of Allowance received for U.S. Appl. No. 13/298,042, dated Aug. 11, 2014, 7 pages.
Notice of Allowance received for U.S. Appl. No. 13/298,042, dated Nov. 13, 2014, 5 pages.
Notice of Allowance received for U.S. Appl. No. 14/561,107, dated Mar. 31, 2015, 7 pages.
Corrected Notice of Allowance dated Jun. 9, 2017, for U.S. Appl. No. 14/920,860, filed Oct. 22, 2015, 2 pages.
Written Opinion received for PCT Patent Application No. PCT/US2015/57019, dated Feb. 11, 2016, 6 pages.
Written Opinion received for PCT Patent Application No. PCT/US2015/57021, dated Feb. 10, 2016, 5 pages.
Boberg; Experience in clinical examination of corneal sensitivity: corneal sensitivity and the naso-lacrimal reflex after retrobulbar anaesthesia; The British Journal of Ophthalmology; 39(12); pp. 705-726; Dec. 1955.
Calonge; The treatment of dry eye; Survey Ophthalmology; 45(2); pp. S227-S239; Mar. 31, 2001.
Elsby et al.; Lacrimal secretion in the cat; Br. J. Pharmac. Chemother; 29(1); pp. 1-7; Jan. 1967.
Ruskell, Gordon L.; Distribution of pterygopalatine ganglion efferents to the lacrimal gland in man; Experimental Eye Research; 78(3); pp. 329-335; Mar. 2004.
Lora et al.; Lacrimal nerve stimulation by a neurostimulator for tear production; ARVO 2009 Annual Meeting; Fort Lauderdale, FL; Program/Poster # 4244/D847; Presented May 6, 2009.
Roessler et al.; Implantation and explantation of a wireless epiretinal retina implant device: observations during the EPIRET3 prospective clinical trial; Invest Ophthalmol Vis Sci; 50(6):3003-3008; Jun. 2009.
Velikay-Parel et al.; Perceptual threshold and neuronal excitability as long-term safety evaluation in retinal implants (Meeting Abstract); Association for Research in Vision and Ophthalmology, Inc. Annual Meeting; 4pgs; May 3, 2011 (printed from http://www.abstractsonline.com/Plan/ViewAbstract.aspx?sKey=00d4c2e2-2814-48d9-b493-38f4761ab4ca&cKey=9d81879a-9b1d-49c2-aff4-89d0bfd86584&mKey=6f224a2d-af6a-4533-8bbb-6a8d7b26edb3 on Dec. 30, 2013).
Australian Examination Report dated Feb. 28, 2014 for AU Application No. 2011328900; 3 pgs.
Australian Examination Report dated Mar. 17, 2014 for AU Application No. 2012239966; 6 pgs.
Extended European Search Report dated Oct. 21, 2016 for EP Application No. 14778719.6; 8 pgs.
International Search Report dated Feb. 23, 2012 for PCT International Application No. PCT/2011/060989; 4 pgs.
Written Opinion of the International Search Authority dated Feb. 23, 2012 for PCT International Application No. PCT/2011/060989; 12 pgs.
International Search Report dated Oct. 26, 2012 for PCT International Application No. PCT/2012/032629; 4 pgs.
Final Office Action dated Feb. 1, 2017, for U.S. Appl. No. 14/920,852, filed Oct. 22, 2015, 20 pages.
Final Office Action dated Mar. 10, 2017, for U.S. Appl. No. 14/920,847, filed Oct. 22, 2015, 12 pages.
Non-Final Office Action dated Dec. 6, 2016, for U.S. Appl. No. 14/816,846, filed Aug. 3, 2015, 13 pages.
Notice of Allowance dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Mar. 28, 2017, for U.S. Appl. No. 14/207,072, filed Mar. 12, 2014, 8 pages.
Written Opinion of the International Search Authority dated Oct. 26, 2012 for PCT International Application No. PCT/2012/032629; 8 pgs.

* cited by examiner

SYSTEMS AND METHODS FOR TREATMENT OF DRY EYE

CROSS REFERENCE TO RELATED APPLICATIONS

The present application is a continuation of U.S. patent application Ser. No. 14/816,846, filed on Aug. 3, 2015, titled "SYSTEMS AND METHODS FOR TREATMENT OF DRY EYE," now U.S. Patent Application Publication No. 2015/0335900/A1, which is a continuation of U.S. patent application Ser. No. 14/561,107, filed on Dec. 4, 2014, titled "SYSTEMS AND METHODS FOR TREATMENT OF DRY EYE," now U.S. Pat. No. 9,095,723, which is a continuation of U.S. patent application Ser. No. 13/298,042, filed on Nov. 16, 2011, titled "SYSTEMS AND METHODS FOR TREATMENT OF DRY EYE," now U.S. Pat. No. 8,918,181, which claims the benefit of U.S. Provisional Patent Application Nos. 61/414,293, filed on Nov. 16, 2010, titled "METHOD AND SYSTEM FOR TREATING DRY EYE;" 61/433,645, filed Jan. 18, 2011, titled "TREATMENT FOR DRY EYE DISEASE;" 61/433,649, filed Jan. 18, 2011, titled "SYSTEMS FOR TREATING DRY EYE;" and 61/433,652, filed Jan. 18, 2011, titled "LEADS AND ELECTRODES FOR TREATING DRY EYE." The foregoing applications are hereby incorporated by reference herein in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to a stimulation system and methods of use thereof. In various respects, the invention is directed to the devices and techniques for stimulating the anatomical structures related to the process of lacrimation for the treatment of dry eye syndrome.

BACKGROUND

Severe Dry Eye is a debilitating disease that affects millions of patients worldwide and can cripple some patients. Millions of these individuals suffer from the most severe form. This disease often inflicts severe ocular discomfort, results in a dramatic shift in quality of life, induces poor ocular surface health, substantially reduces visual acuity and can threaten vision. Patients with severe Dry Eye develop a sensitivity to light and wind that prevents substantial time spent outdoors, and they often cannot read or drive because of the discomfort. There is no cure for Dry Eye disease, and current treatment options provide little relief for those suffering from severe conditions. Current options include artificial tears, punctal plugs, humidity goggles, topical cyclosporine, and tarsorrhaphy. None of these treatments provides sufficient relief or treatment of the disease. What is needed is a system for restoring adequate tear production in patient's having severe Dry Eye disease.

SUMMARY OF THE DISCLOSURE

In an embodiment, the present invention relates to a microstimulator for treating conditions of the eye having a length of about 0.6 cm to about 1.5 cm and a width of about 1 mm to about 1.5 mm and comprising a passive stimulation circuit. The microstimulator may be conformable and flexible and may have one or more fixation elements. The one or more fixation elements may include one or more hooks, barbs, and anchors. The microstimulator may have one or more coatings which may be adhesive and bioabsorbable.

The passive stimulation circuit may include a tank circuit and have one or more electrical safety features. The electrical safety features may include one or more current limiting rectifiers and one or more zener diodes. The electrical safety features may include a voltage limiting circuit to limit the voltage emitted by the stimulation component. The electrical safety feature may also include a current limiting circuit to limit the current emitted by the stimulation component and a charge output limiting circuit to limit the charge emitted by the stimulation component.

The passive stimulation circuit within a microstimulator may also include a variable resistive element, a variable capacitive element and one or more electrodes. The one or more electrodes of the passive stimulation circuit may be contact points, may be nestled within the microstimulator, may be coupled to a flexible lead, and may be coupled to a rigid lead. The one or more electrodes may contain platinum, iridium, platinum iridium, iridium oxide, titanium nitride, tantalum, or combinations thereof.

The microstimulator may be coupled to a controller and be hermetically sealed. The microstimulator may be injectable into a patient's eye with a 12 or larger gauge needle. The microstimulator may have one or more features to facilitate minimally invasive retrieval. The length and width of the microstimulator may be selected to permit placement of a portion of the microstimulator adjacent to the lacrimal gland. The length and width of the microstimulator may also be selected to permit placement of the entire microstimulator adjacent to the lacrimal gland and to permit placement of the microstimulator on, partially in, within or about the lacrimal gland.

In an embodiment, a method for treating dry eye by stimulating one or more nerves that innervate lacrimal gland tissue includes implanting a microstimulator adjacent to the lacrimal gland and applying stimulation to the lacrimal gland. The microstimulator may be adjacent the lacrimal gland and fully implanted within an orbit of a patient's eye. The microstimulator may be adjacent and directly contacting the lacrimal gland. The microstimulator may be adjacent to and at least partially penetrating into the lacrimal gland. The microstimulator may be adjacent to and fully implanted into or completely within the lacrimal gland. Adjacent to the lacrimal gland may include about, within or partially in the lacrimal gland. The microstimulator may be fully implanted within the orbit of the eye.

The stimulation provided by the microstimulator may selectively stimulate one or more nerves that innervate the lacrimal gland. The stimulation may selectively stimulate the one or more nerves that innervate the lacrimal gland without moving the eye in the vertical or horizontal direction, or rotationally, without stimulating the ocular muscles, and without stimulating the superior rectus, lateral rectus, levator palpebrae superioris, retina or corresponding motor nerves. The autonomic efferent fibers may be selectively stimulated over the sensory afferent fibers or the A-delta pain fibers or over the C pain fibers. In various embodiments, the stimulation may stimulate only the one or more nerves that innervate the lacrimal gland.

After the implanting step, the microstimulator may be implanted into the fossa for the lacrimal gland and may conform to the fossa for the lacrimal gland after implantation. The microstimulator may conform to an exterior aspect of a lacrimal gland after implantation. The implanting step may further include conforming the microstimulator to an exterior aspect of the lacrimal gland. After the implanting step, the microstimulator may conform to an exterior aspect of the fossa for the lacrimal gland.

The microstimulator may be implanted using a 12 or larger gauge needle. The microstimulator may be loaded into a 12 or larger gauge needle, a microstimulator needle tip may be inserted using an anatomical landmark at the corner of the eye, the needle may be positioned in proximity to the lacrimal gland, and the microstimulator may be deployed using the needle. The anatomical landmark may be the temporal aspect of the orbit into the superior lateral aspect of the orbit and through the orbital septum. The stimulation may include a current having a pulse amplitude between about 500 μA to about 25 mA. The stimulation may include a pulse amplitude, a pulse width, and a pulse frequency, and one or more of the pulse amplitude, pulse width, or pulse frequency which may be varied over the treatment period. The stimulation may have a pulse frequency between about 2 Hz to about 270 Hz or between about 30 Hz to about 40 Hz. The stimulation may include a current having a pulse width between about 50 μsec to about 2700 μsec.

The implanting step may further include identifying an insertion point for implantation based upon a feature of the orbit. The stimulation may be delivered in bursts and adjusted in response to a measured variable. The stimulation may include a current having a pulse width between about 500 μsec to about 1000 μsec. A controller may be positioned in proximity to the microstimulator and may generate a magnetic field. The magnetic field may be adjusted based on input from the user and based on the degree of coupling to the microstimulator. The magnetic field may be generated in bursts and coupled to the microstimulator to generate the stimulation. The magnetic field may have a frequency of about 10 kHz to about 100 MHz. The magnetic field may have a frequency of about 100 kHz to about 5 MHz.

In an embodiment, a system for treating dry eye may include a microstimulator configured for implantation into an orbit of an eye and a controller for generating a magnetic field to couple to the microstimulator. The controller may be housed within a hand-held device. The controller may be at least partially contained within and coupled to an adhesive. The controller may be flexible and conformable. The controller may be coupled to, or at least partially contained within, a flexible or conformable material. The microstimulator may have a length of about 0.6 cm to about 1.5 cm and a width of about 1 mm to about 1.5 mm and may include a passive stimulation circuit configured to receive the magnetic field generated by the controller. The microstimulator may be flexible, conformable, and capable of detecting one or more operating parameters of the microstimulator. At least part of the controller may be disposable and rechargeable. The controller may be coupled to, or at least partially contained within, an eyeglass frame, a wrist watch, or other object.

In an embodiment, a method for treating dry eye by stimulating one or more nerves that innervate lacrimal gland tissue may include positioning one or more stimulation electrodes adjacent to the lacrimal gland and applying stimulation to the lacrimal gland. A microstimulator may be adjacent the lacrimal gland fully implanted within an orbit of a patient's eye. The microstimulator may be adjacent and directly contacting the lacrimal gland, adjacent to and at least partially penetrating into the lacrimal gland, and adjacent to and fully implanted into or completely within the lacrimal gland. Adjacent to the lacrimal gland may be about, within or partially in the lacrimal gland. The microstimulator may be fully implanted within the orbit of the eye. The one or more electrodes are electrically coupled to a pulse generator, which may be implantable. The pulse generator may be implantable in proximity to the one or more stimulation electrodes. The pulse generator may be implantable in proximity to the temporal bone, a subclavicular pocket, and a subcutaneous abdominal pocket. The method may further include positioning a controller in proximity to the pulse generator.

In an embodiment, a microstimulator may include a coil, a housing, and a pair of electrodes. The coil may be formed from a wire having a length turned into a plurality of windings and responsive to an induced field to produce an output signal. The microstimulator may be electrically coupled to receive the output from the coil and produce a signal responsive to the output. The housing may encompass the circuit and the coil, and may be adapted and configured for placement within an orbit and adjacent an eye within the orbit. The pair of electrodes may extend from the housing and be configured to receive the signal.

The pair of electrodes and the housing may be shaped for injection through the lumen of a needle. The housing may be configured for placement adjacent to a lacrimal gland, within an orbit to permit selective stimulation of a lacrimal gland with the signal, and within a fossa near the lacrimal gland to position the pair of electrodes on, in or about a lacrimal gland.

The housing may be configured for placement in proximity to a lacrimal gland without being in proximity to a muscle of the eye. The housing may have a curvature conforming at least partially to the curvature of a fossa for the lacrimal gland, or a curvature conforming at least partially to an exterior aspect of a lacrimal gland.

The microstimulator may further include a second coil, a second rectifying and tuning circuit. The second coil may be within the housing and oriented nearly orthogonal to the second coil. The second rectifying and capacitive circuit may be within the housing and coupled to the second coil, such that the second rectifying and capacitive circuit is configured to produce a second signal. The selector switch may be within the housing and connected to receive the first signal and the second signal and supply one of the first signal and the second signal to the pair of electrodes. The selector switch may determine which one of the first signal and the second signal to send to the electrodes based on a comparison of the first signal and the second signal. Current from the two signals may be summed without the use of a selector switch. The signal from the coil may have a frequency corresponding to the induced field, which may be generated from an external coil through mutual inductance. The induced field may be generated by an external controller.

The signal generated in the coil has a frequency about equal to the frequency of the induced field generated by the external controller. The induced field generated by the external controller may have a frequency based on user input. The external controller may be contained within a hand-held device and may be disposable. The external controller may be contained within one of an adhesive patch, a pair of eye glasses, and a head set. The circuit may include a capacitor for storing voltage and a diode to rectify a current signal. The circuit may include a rectifying circuit that may include a diode and a resistor connected in parallel. The signal may have a voltage with an amplitude of between 0.1V and 0.25V, a current with an amplitude between 10 μA and 25 mA, and an alternating current with a frequency of 2 Hz to 1000 Hz. The pair of electrodes may be connected to leads, which may include tines.

In an embodiment, a method of implanting a microstimulator adjacent the eye may include inserting an access device percutaneously into an orbit of an eye. A microstimulator may be advanced through the access device into a position in proximity to the superior lateral aspect of the orbit. A stimulation signal may be applied to a portion of the eye with the microstimulator. Before the inserting step, an insertion point may be inserted for the access device based on the insertion point's relation to a feature on the orbit. After the advancing, the microstimulator may be positioned within a fossa of the lacrimal gland, and at least one electrode of the microstimulator may be positioned on, in or adjacent to a lacrimal gland, and an electrode of the microstimulator is positioned on, in or adjacent a lacrimal gland.

Tear production may be increased in the eye. Vasodilation of the lacrimal gland may occur unilaterally or bilaterally. After advancing, an electrode of the microstimulator may be positioned on, in or adjacent to a neural structure associated with a lacrimal gland. During the applying, the signal only stimulates a lacrimal gland, the signal may selectively stimulate a lacrimal gland over a muscle of the eye, or the signal is selected to stimulate a lacrimal gland without stimulating a muscle fiber of the eye. After the advancing, an electrode of the microstimulator is positioned adjacent to a neural structure associated with a lacrimal gland and spaced apart from a muscle of the eye. The muscle of the eye may be a rectus muscle or an oblique muscle or a levator palpebrae muscle. The microstimulator may be adjacent a lacrimal gland and spaced apart from a superior rectus muscle or a lateral rectus muscle or a levator palpebrae muscle. The signal may stimulate a lacrimal gland without activating a rectus muscle or an oblique muscle or a levator muscle in proximity to the lacrimal gland.

In an embodiment, a method for using an microstimulator may include receiving an microstimulator at the orbit of a patient's eye. A magnetic field may be received by the microstimulator from an external power source such as a controller. A current may be generated by the microstimulator from the magnetic field. The current may be applied to the patient to produce tears in the patient's eye or vasodilation of the lacrimal gland.

In an embodiment, a method for using a microstimulator may include implanting a stimulation device within a patient's orbit. A controller with a power source may be placed external to the patient's skin and in communication with the microstimulator. A magnetic field may be applied to the microstimulator from the controller. A current may be generated in the microstimulator from the magnetic field. The current may be applied to produce tears in the patient's eye.

In an embodiment, a system for treating a patient with dry eye syndrome may include a microstimulator and a controller. The microstimulator may be responsive to a magnetic field and placed within an orbit of a patient's eye. The microstimulator may be configured to generate a current based on the magnetic field and apply the current to a patient to produce tears in the patient's eye. The controller may be configured to generate the magnetic field and be placed at a location near the microstimulator.

In an embodiment, a method for treating a patient with dry eye syndrome may begin with insert a microstimulator within an orbit of a patient's eye using a positioning device. A controller, which may include a power source, may be placed external to a patient's skin and in proximity to the microstimulator. A magnetic field may be applied to the microstimulator by the controller. A current may be generated by the microstimulator from the magnetic field. The current may then be applied to a patient to produce tears in the patient's eye.

In an embodiment, a method for using an microstimulator may begin with connecting an microstimulator to a multi-electrode lead positioned on, in or adjacent a lacrimal gland. One or more electrodes may be selected from the multi-electrode lead to activate tear production in a patient's eye.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
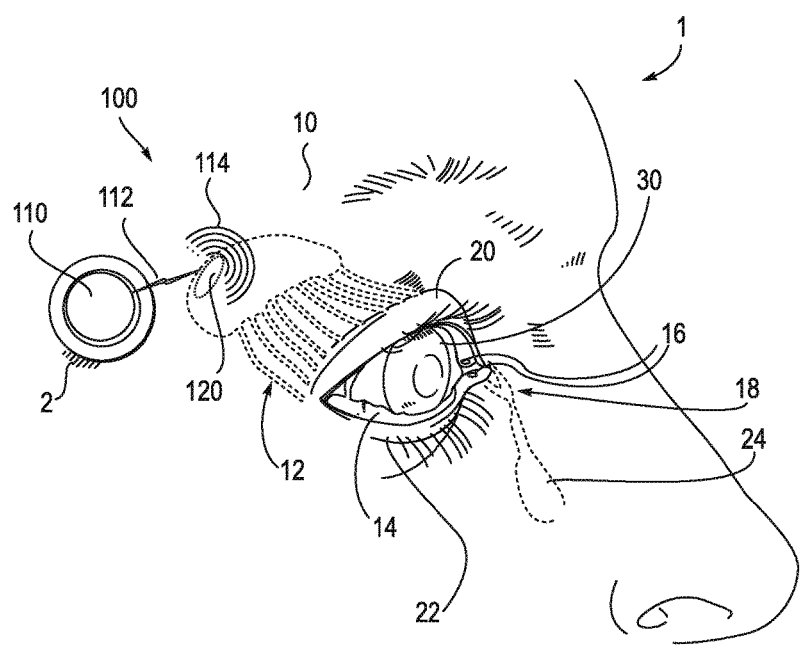
FIG. 1 is a schematic drawing of the front side view of a patient's lacrimal apparatus that includes a controller and a microstimulator.

The present invention relates to a stimulation system for stimulating anatomical targets in a patient for treatment of dry eye. The stimulation system may include a controller and a microstimulator. The controller may be implemented external to or internal within the microstimulator. In various embodiments, the components of the controller and microstimulator may be implemented in a single unit or in separate devices. When implemented separately, the controller and microstimulator may communicate wirelessly or via a wired connection. The microstimulator may generate pulses from a signal received from the controller and apply the signal via one or more electrodes to an anatomical target. In various embodiments, the microstimulator does not have any intelligence or logic to shape or modify a signal, but rather is a passive device configured to generate a pulse based on a signal received from the controller. Unlike other implantable stimulation devices, the passive elements of the microstimulator of the present invention allow for an inexpensive implementation. The present microstimulator does not include numerous integrated components such as ASICs, pieces of silicon and other expensive components. In contrast to having a battery, ASIC and other components, the present microstimulator only has a dissipation circuit to deliver a charge. In various embodiments, the microstimulator includes intelligence to shape or modify a signal. In various embodiments, waveforms having different frequency, amplitude and period characteristics may stimulate different anatomical targets in a patient.

An anatomical target may include a nerve, tissue, gland or other structure of a patient involved in the process of lacrimation or glandular vasodilation that may be stimulated by a microstimulator. For example, the anatomical targets may include, but are not limited to, a lacrimal gland, one or more meibomian glands, lacrimal ducts, parasympathetic nerves, fibers and neurites, sympathetic nerves, fibers and neurites, rami lacrimales, lacrimal nerve, perivascular nerves of lacrimal artery and branches thereof, nerve fibers innervating the meibomian glands, myoepithelial cells of the lacrimal gland, acinar cells of the lacrimal gland, ductal cells of the lacrimal gland.

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as defined by the appended claims.

FIGS. 1-17 discuss and relate to a microstimulator. Each reference to a microstimulator is intended to be illustrative. A microstimulator of the present invention may be implemented as any of the illustrative microstimulators, a combination of portions of each illustrative microstimulator, or with additional or fewer components.

FIG. 1 is a schematic drawing of the front side view of a patient's lacrimal apparatus that includes a controller and a microstimulator. FIG. 1 includes an eye 30 having an upper lid 20 and lower lid 22. The lacrimal (i.e. lachrymal) apparatus is the physiological system containing the structures of the orbit for tear production and drainage. The lacrimal apparatus includes a lacrimal gland 10, ducts 12, puncta 16, lacrimal ducts 18, and nasolacrimal duct 24. The lacrimal gland 10 secretes tears 14 (lacrimal fluid) which flow through the ducts 12 into the space between the eye 30 and lids 20 and 22. When the eye 30 blinks, tears 14 are spread across the surface of the eye 30. The tears 14 collect in the lacrimal lake (not shown), and are drawn into the puncta 16 by capillary action. The tears 14 flow through the lacrimal canaliculi (not shown) at the inner corner of the lids 20 and 22, enter the lacrimal ducts 18 and drain through to the nasolacrimal duct 24, and finally continue into the nasal cavity.

A microstimulator 120 may be positioned within an orbit as shown in FIG. 1 and adjacent to eye 30 within the orbit. The microstimulator 120 may be placed on, in or adjacent the lacrimal gland 10. In various embodiments, the microstimulator 120 is implanted into the fossa of the lacrimal gland (illustrated in FIG. 2). The microstimulator 120 may stimulate one or more nerves that innervate the lacrimal gland 10. Microstimulator 120 may receive a waveform 112 and may provide an output signal 114 for stimulating one or more anatomical targets of a patient. In various embodiments, the microstimulator 120 selectively stimulates one or more nerves that innervate the lacrimal gland 10. Additionally, the microstimulator 120 may stimulate one or more nerves that innervate the lacrimal gland 10 indirectly as opposed to directly.

Direct stimulation of a nerve includes delivering low amplitude electrical stimulation via electrodes that are in direct contact with the nerve to be stimulated. The electrodes may be located on the sheath of the axon or away from the portion of the nerve that innervates tissue or gland. An example of a direct nerve stimulator is a nerve cuff which includes electrodes carried on the inside walls of a cylindrical polymeric sheath. The nerve cuff is wrapped around the nerve to bring the electrodes into direct contact with an isolated portion of a nerve to be stimulated. Indirect stimulation of a nerve includes delivering low amplitude electrical stimulation via electrodes that are in close proximity, but not in direct contact, with the nerve to be stimulated. Nerves that are in a bundle, plexus or innervating tissue or a gland are not isolated from other nerves or structures. Target nerves or structures that are not isolated may stimulated indirectly by using electrical selectivity.

The lacrimal gland 10 may be innervated by several nerves. The nerves may include the rami lacrimales, the lacrimal nerve, perivascular nerves of lacrimal artery, and sympathetic nerves fibers and neurites which innervate the lacrimal gland and its associated vasculature.

A controller 110 may provide power to the microstimulator 120. The controller 110 may provide power wirelessly or through a wired connection to the microstimulator 120. The power may be provided through a magnetic field, electronic signal or in some other manner. The controller 110 may be implemented external to the patient's skin 2 or implanted into the patient 1. The controller 110 and the microstimulator are discussed in more detail with respect to FIGS. 3-8.

Figure 2A:
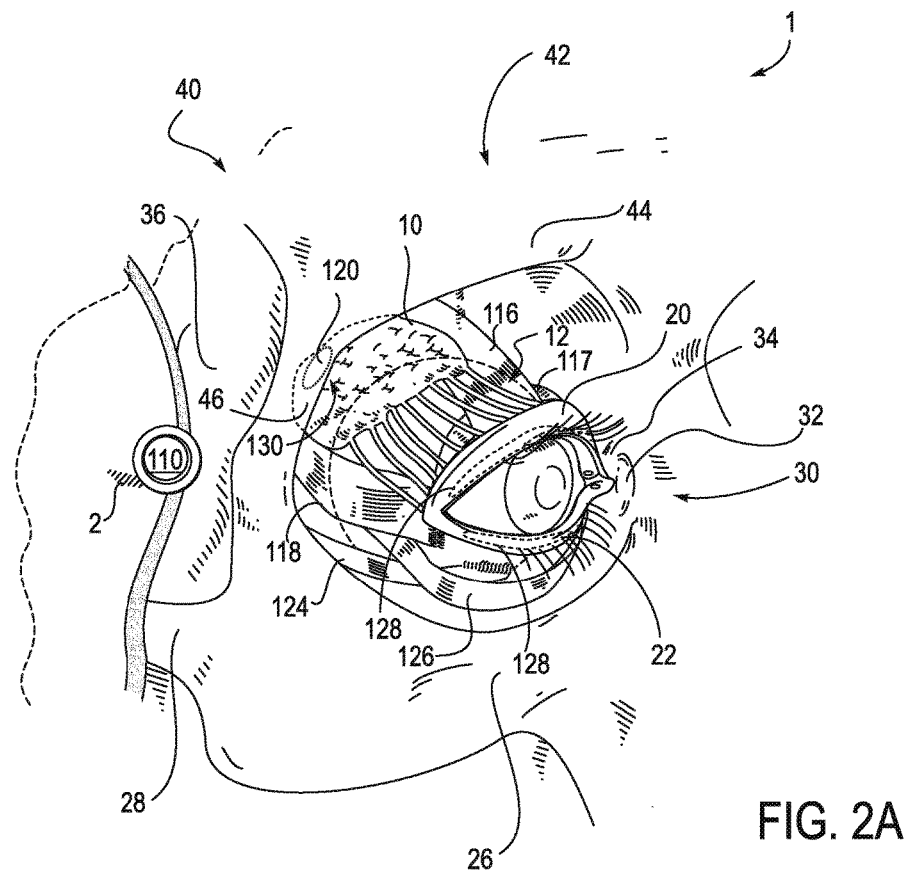
FIG. 2A is a perspective view of an eye within the orbit of a patient's skull that includes a controller and a microstimulator.

FIG. 2A is a perspective view of an eye within the orbit of a patient's skull that includes a controller and a microstimulator. FIG. 2A includes the eye 30, upper lid 20, lower lid 22, lacrimal gland 10, ducts 12, microstimulator 120, and controller 110 as shown in FIG. 1. The rim of the upper lid 20 and the lower lid 22 contain the meibomian glands 128. The meibomian glands 128 are sebaceous glands responsible for the supply of meibum which is an oily substance consisting of lipids that slows evaporation of the eye's tear film.

The posterior lacrimal crest 34 is a vertical ridge that divides the orbital surface of the lacrimal bone into two parts. In front of the posterior lacrimal crest 34 is a longitudinal groove which unites with the frontal process 46.

There are two bony depressions in the orbital cavity that may be referred to as the lacrimal fossa. The first is a smooth, concave shallow depression located on the inferior surface of each orbital plate of the frontal bone. This depression houses the lacrimal gland and is referred to as the fossa for the lacrimal gland 130. The second is a smooth, more deeply concave depression on the lacrimal bone, which forms the medial wall of the orbital cavity. This depression houses the lacrimal sac and is referred to as the fossa for the lacrimal sac 32.

The supraorbital process 44 is a passage in the frontal bone for the supraorbital artery and nerve. The supraorbital process 44 is located on the superior and medial margin of the orbit in the frontal bone. The orbit of the skull 40 is lined with a periosteum (illustrated in FIGS. 2C-J) and contains the eye 30, extraocular muscles for movement of the eye 30, veins (not shown), arteries (not shown), and nerves (not shown) which traverse the orbit into the face and the lacrimal gland 10. The extraocular muscles include the lateral rectus 118, the medial rectus (not shown), the superior rectus 116, inferior rectus 124, superior oblique 117, inferior oblique 126, and levator palpebrae superioris (not shown). The lateral rectus 118 abducts the eye away from the nose and the medial rectus adducts the eye towards the nose. The lateral rectus 118 and medial rectus move the eye only in a horizontal plane. The superior rectus 116, inferior rectus 124, superior oblique 117, and inferior oblique 126 control vertical motion. The levator palpebrae superioris originates on the sphenoid bone 36 and is responsible for elevating the upper lid 20.

The malar process 26 is the rough projection from the maxilla (not shown) that articulates with the zygomatic bone 28. The bones of the skull 40 and the orbit are discussed further in FIG. 2B.

Figure 2B:
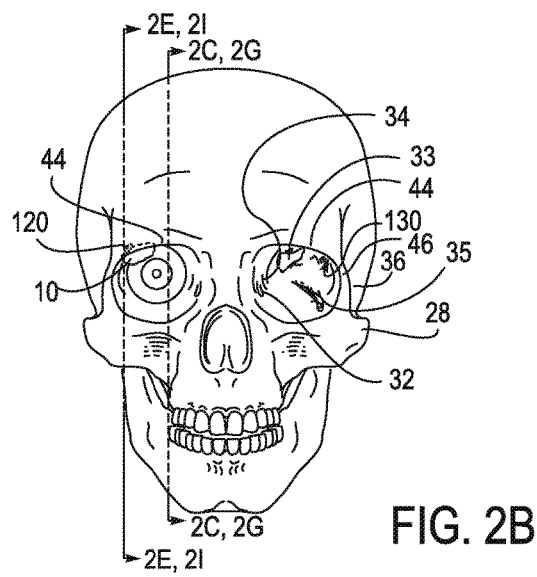
FIG. 2B is a front view of a patient's skull having a microstimulator.

FIG. 2B is a front view of a patient's skull having a microstimulator. The front view of the skull 40 includes a right and left orbit. The right orbit of FIG. 2B emphasizes the approximate position of the microstimulator 120 with respect to the lacrimal gland 10 and the supraorbital process 44 discussed with respect to FIGS. 1 and 2A. The left orbit of FIG. 2B emphasizes the anatomy of the orbit with respect to the bones of the skull 40. Exterior to the left orbit includes the posterior lacrimal crest 34, the supraorbital process 44, the frontal process 46, sphenoid bone 36, and the zygomatic bone 28 as previously discussed with respect to FIGS. 1 and 2A.

The interior of the left orbit includes the superior orbital fissure 33, inferior orbital fissure 35, the fossa for the lacrimal gland 130 and the fossa for the lacrimal sac 32. The structures that enter through the superior orbital fissure 33 include the cranial nerves (CN) III, IV, and VI, lacrimal nerve, frontal nerve, nasociliary nerve, orbital branch of middle meningeal artery, recurrent branch of lacrimal artery, superior orbital vein, and the superior ophthalmic vein. The structures that enter through the inferior orbital fissure 35 include the infraorbital nerve, zygomatic nerve, parasympathetics to the lacrimal gland, infraorbital artery, infraorbital vein, and inferior ophthalmic vein branch to pterygoid plexus.

The structures entering through the superior orbital fissure 33 and the inferior orbital fissure 35 may be stimulated by the microstimulator 120. In various embodiments, the stimulation may be selectively applied to these structures by varying the pulse amplitude, pulse width, pulse frequency or other properties of the stimulation signal.

Figure 2C:
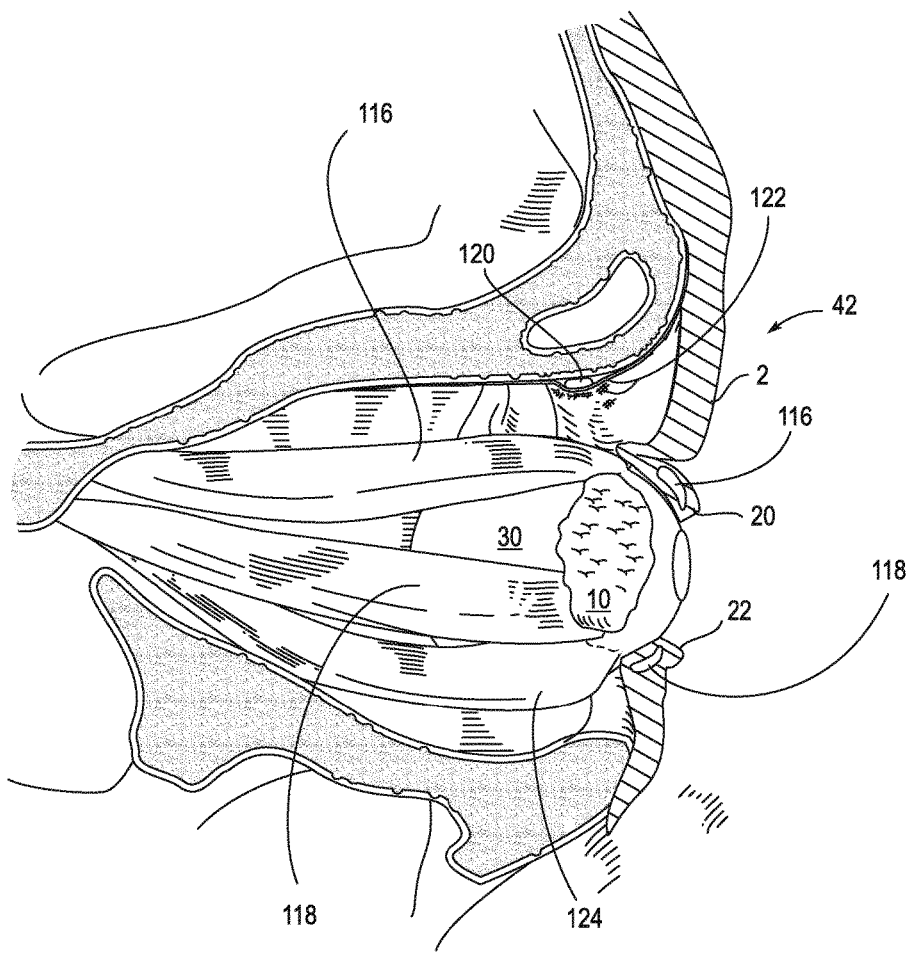
FIG. 2C is a section medial view of an eye within the orbit of a patient's skull.

FIG. 2C is a section medial view of an eye within the orbit of a patient's skull. The view of FIG. 2C corresponds to the view line 2C illustrated in FIG. 2B. FIG. 2C includes the eye 30 with upper lid 20 and lower lid 22, superior rectus 116, lateral rectus 118, inferior rectus 124, the lacrimal gland 10, and the microstimulator 120 of FIG. 2A. The orbital process 42 of the zygomatic bone is a thick, strong plate, projecting backward and medialward from the orbital margin. The microstimulator 120 may be positioned between the portion of the bone forming the fossa for the lacrimal gland 130 and the periosteum 122. The periosteum 122 of the orbit of a healthy eye may be tightly attached. In cases of a diseased eye, the periosteum 122 may be loosely attached and raised from the bone beneath.

Figure 2D:
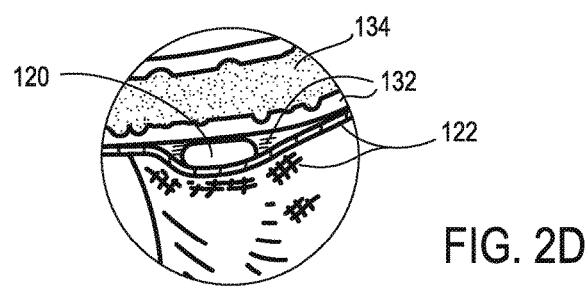
FIG. 2D is an enlarged section view of the microstimulator in the orbit of FIG. 2C.

FIG. 2D is an enlarged section view of the microstimulator in the orbit of FIG. 2C. FIG. 2D includes the microstimulator 120 positioned between the portion of the bone forming the fossa for the lacrimal gland 130 and the periosteum 133. The bone includes cortical tissue 132 and cancellous tissue 134. Cortical 132 and cancellous 134 are two types of osseous tissue that form bone.

Figure 2E:
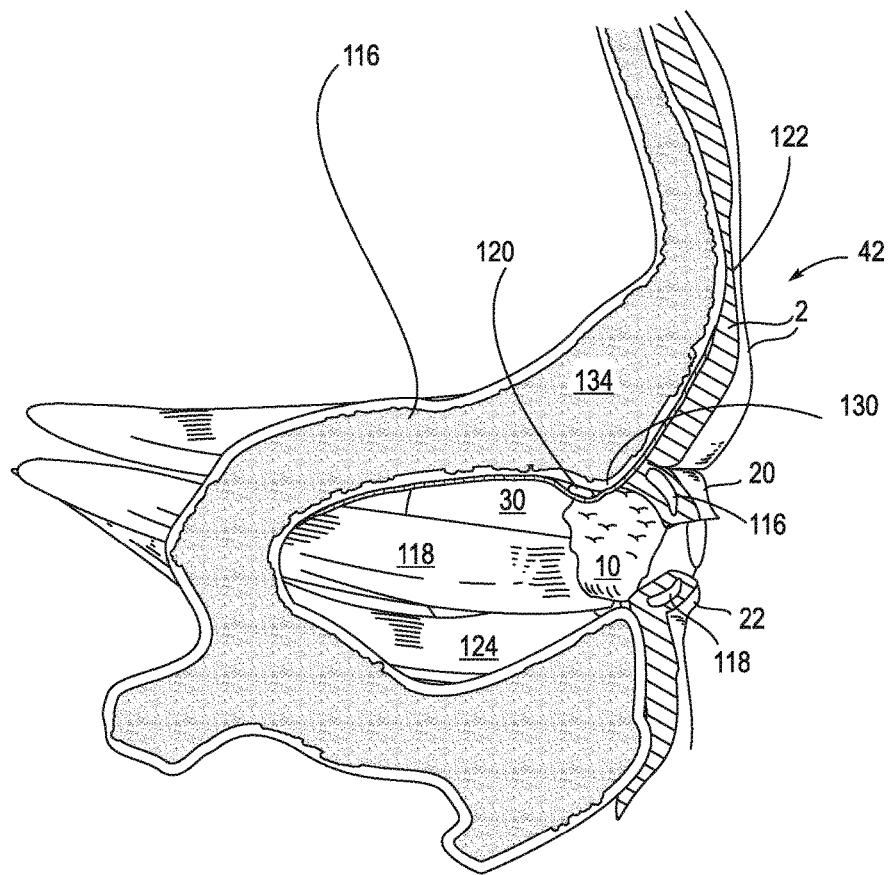
FIG. 2E is another section medial view of an eye within the orbit of a patient's skull.

FIG. 2E is another section medial view of an eye within the orbit of a patient's skull. The view of FIG. 2E corresponds to the view line 2E illustrated in FIG. 2B. FIG. 2C is lateral and more medial than FIG. 2E. FIG. 2E includes the eye 30 with upper lid 20 and lower lid 22, superior rectus 116, lateral rectus 118, inferior rectus 124, the lacrimal gland 10, and the microstimulator 120 of FIGS. 2A-D. FIG. 2E also includes the fossa for the lacrimal gland 130. The microstimulator 120 is shown positioned between the periosteum 133 and the portion of the bone forming the fossa for the lacrimal gland 130 as in FIGS. 2C and 2D.

Figure 2F:
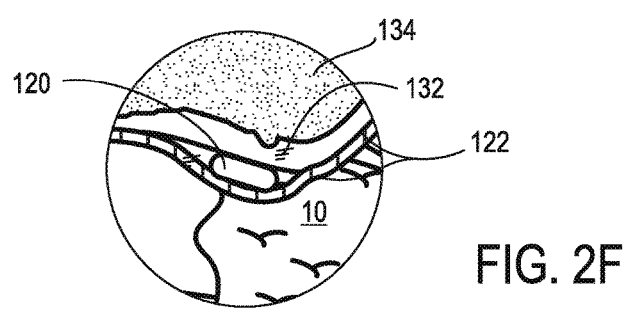
FIG. 2F is another enlarged section view of the fossa for the lacrimal gland having a microstimulator.

FIG. 2F is another enlarged section view of the fossa for the lacrimal gland 130 having a microstimulator. FIG. 2F includes the microstimulator 120 positioned between the portion of the bone forming the fossa for the lacrimal gland 130 and the periosteum 133 adjacent the lacrimal gland 10. Cortical 132 and cancellous 134 of FIGS. 2C-D are also illustrated in FIG. 2F.

Figure 2G:
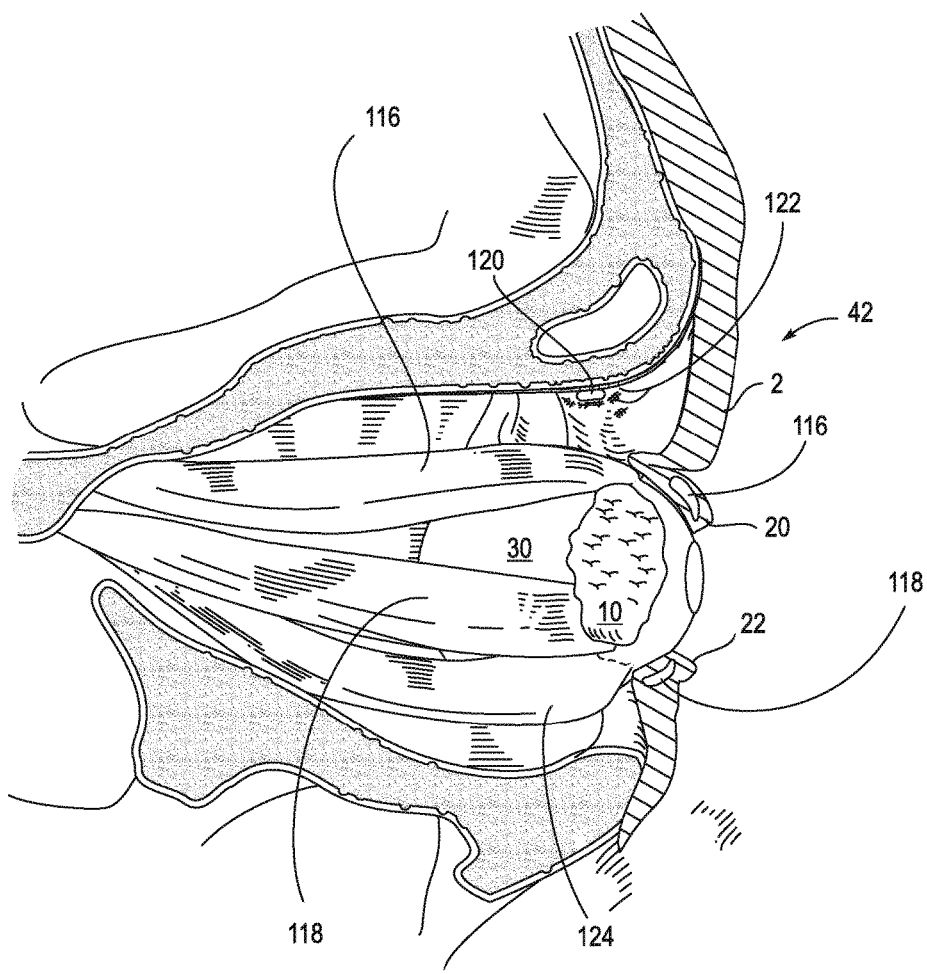
FIG. 2G is another section medial view of an eye within the orbit of a patient's skull.
Figure 2H:
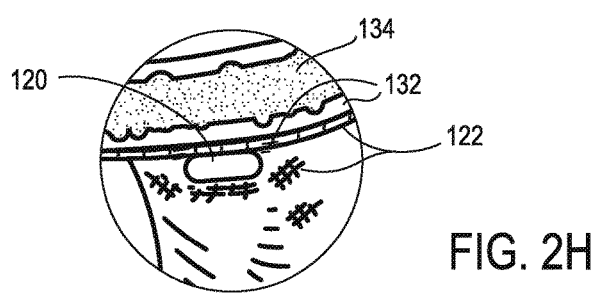
FIG. 2H is another enlarged section view of the inferior edge of the superior orbit having a microstimulator.

FIG. 2G is another section medial view of an eye within the orbit of a patient's skull. The view of FIG. 2G corresponds to the view line 2G illustrated in FIG. 2B. FIG. 2H is another enlarged section view of the inferior edge of the superior orbit having a microstimulator. FIGS. 2G-H are similar to FIGS. 2C-D except that the microstimulator is shown positioned between the periosteum 133 and the lacrimal gland 10. The lacrimal gland 10 is illustrated in the more medial view of FIGS. 2I-J.

Figure 2I:
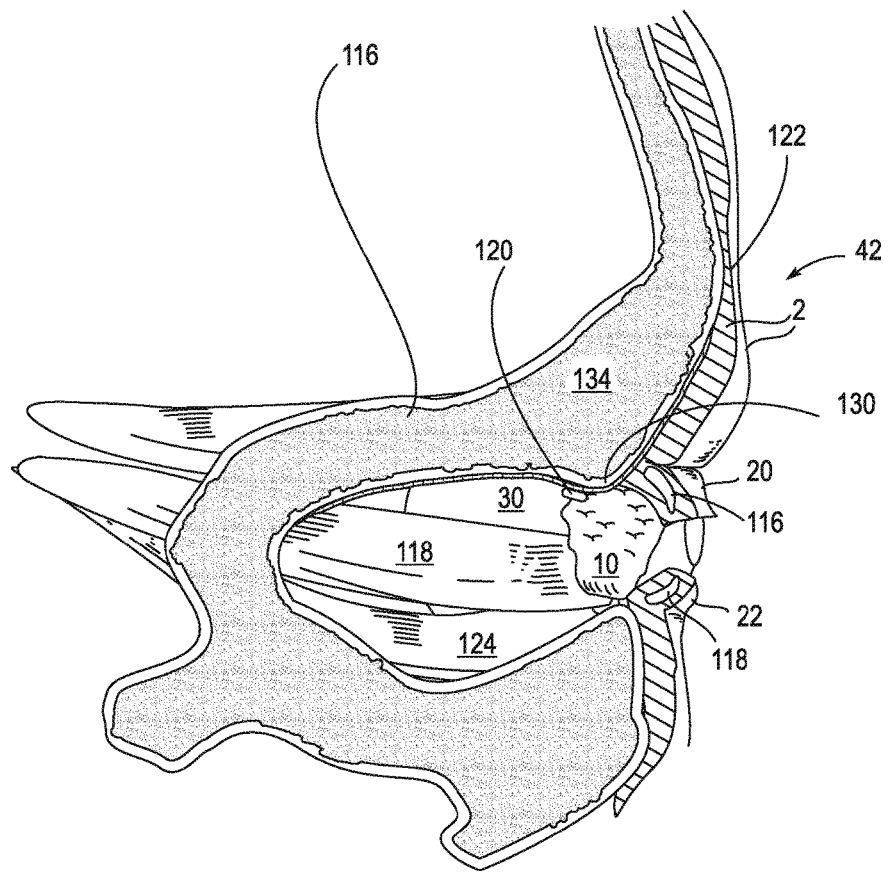
FIG. 2I is another section medial view of an eye within the orbit of a patient's skull.
Figure 2J:
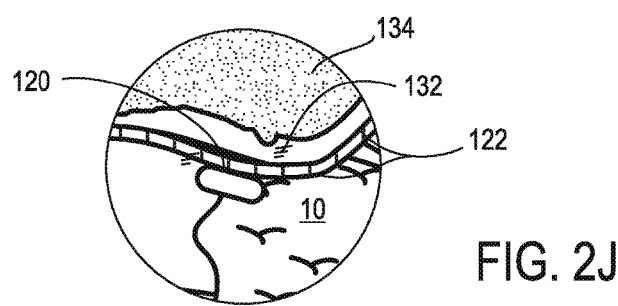
FIG. 2J is a another enlarged section view of the superior orbit having a microstimulator as implanted in FIG. 2I

FIG. 2I is another section medial view of an eye within the orbit of a patient's skull. The view of FIG. 2I corresponds to the view line 2I illustrated in FIG. 2B. FIG. 2J is another enlarged section view of the inferior edge of the superior orbit having a microstimulator. FIGS. 2I-J are similar to FIGS. 2E-F except that the microstimulator is shown positioned between the periosteum 133 and the lacrimal gland 10.

A stimulation system may include a controller and a microstimulator. The components of the controller and microstimulator may be implemented as a single device or separately. When implemented separately, the controller and a microstimulator may communicate wirelessly or via a wired connection. FIGS. 1, 2A, 3-7 illustrate embodiments of a stimulation system with various configurations of a controller and a microstimulator. The controller may be contained within an adhesive. For example, the controller may be attached to a bandage or flexible band aid designed to conform to an outer surface of a patient's skin. In various embodiments, the color of the adhesive may be designed to be visually appealing such as matching a patient's skin tone or translucent. In various embodiments, the controller may be at least partially contained within the adhesive. The adhesive may have a thin profile and may be embedded in a polymer. The polymer may be integrated with a surface of the adhesive. The adhesive may be mounted to a surface of a flexible substrate. The flexible substrate may contain components such as the controller mounted to another surface of the substrate. The components may be coated and potted within the substrate, and may be selected for the bandage such that they are not subjective to eddy currents. The controller may also be coupled to the adhesive or coupled to or at least partially contained within a flexible or conformable material. The controller may further be coupled to or at least partially contained within a wrist watch. The controller may be disposable. The controller may be rechargeable.

Figure 3:
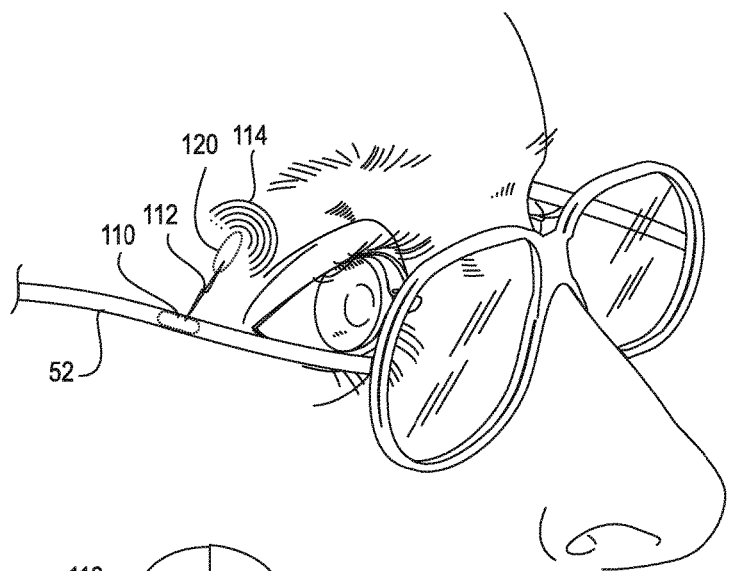
FIG. 3 is an exemplary controller for use with a stimulation system.

FIG. 3 is an exemplary controller for use with a stimulation system. The stimulation system of FIG. 3 includes a controller 110 that is implemented separately from a microstimulator 120. The controller 110 is embedded within a pair of eyeglasses frames 52 worn by a patient in whom the microstimulator is implanted. The controller may also be coupled to at least partially contain within the eyeglass frame. The controller 110 is positioned within the frame to be proximate to the microstimulator 120. From within the eyeglasses frame 52, controller 110 may generate a waveform 112 which may be applied to microstimulator 120, which in turn may be used to generate a signal used to stimulate an anatomical target. The controller may be implemented in a variety of objects in addition to that discussed with respect to FIG. 3 and elsewhere herein.

Figure 4A:
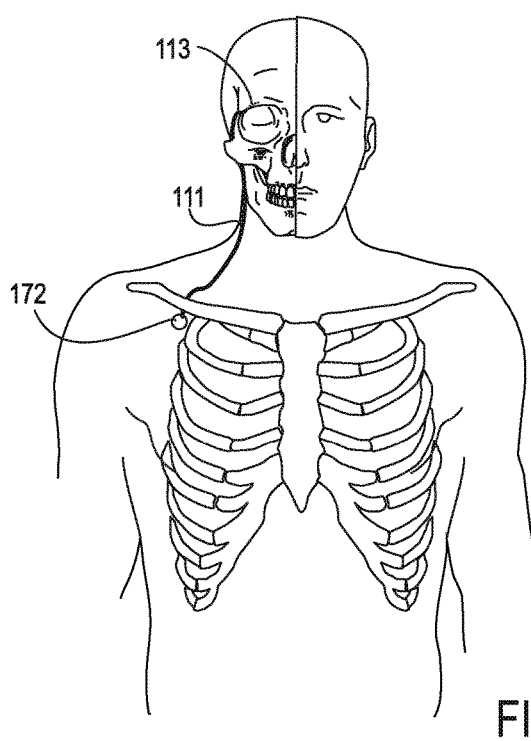
FIG. 4A is an exemplary pulse generator for use with a stimulation system.

FIG. 4A is an exemplary pulse generator for use with a stimulation system. The stimulation system of FIG. 4 includes a pulse generator 172 with a multi-electrode lead. In various embodiments, the electrode lead may be monopolar. The pulse generator may be implemented within the patient, for example near the patients clavicle bone, and thereby form an implantable pulse generator. The leads may extend within the body of the patient from the pulse generator 172 to the microstimulator 120 mounted within the patient's head.

Figure 4B:
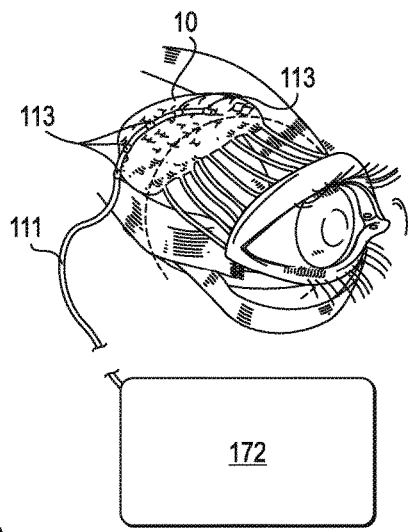
FIG. 4B is an enlarged view of the stimulation system components of FIG. 4A near the eye of the patient.

FIG. 4B is an enlarged view of the stimulation system components of FIG. 4A near the eye of the patient. The stimulation system components of FIG. 4A include electrodes 113 and lead 111. The composition of the electrode may include, but is not limited to, platinum, iridium, platinum iridium, iridium oxide, sputtered iridium oxide, titanium nitride, tantalum, and combinations thereof. Electrodes 113 are attached to lead 111 to form a multi-electrode lead. The multi-electrode lead is positioned such that the electrodes may be adjacent to or in the lacrimal gland. Each of electrodes 113 may be selectively activated to stimulate one or more desired anatomical targets. For example, electrodes 1, 3 and 4 may be activated to stimulate a first anatomical target and electrodes 2 and 5 maybe activated to stimulate a second anatomical target. The one or more anatomical targets may be stimulated by different combinations of electrodes to produce tears in the patient's eye, or to produce vasodilation in the lacrimal gland.

Figure 5:
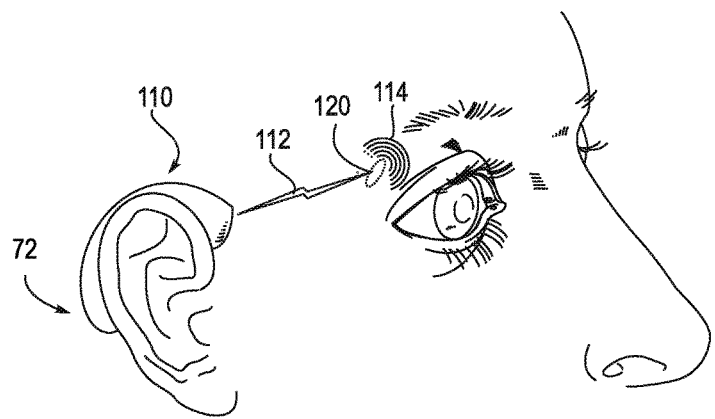
FIG. 5 illustrates a controller with a microstimulator having a passive stimulation circuit.

FIG. 5 illustrates a controller with a microstimulator having a passive stimulation circuit. Controller 110 may be worn over the patient's ear near the mastoid region 72 of the temporal bone as shown in FIG. 5. In various embodiments, the controller 110 may be implemented as an adhesive patch worn behind the ear in the mastoid region 72 of the temporal bone. The controller 110 may wirelessly transmit a waveform 112 to micro stimulator 120. Microstimulator may receive the wireless waveform, which then activates the passive stimulation circuit. The passive stimulation circuit may then process the waveform, for example by generating a rectified signal, and applying the signal to one or more anatomical targets via one or more electrodes.

Figure 6A:
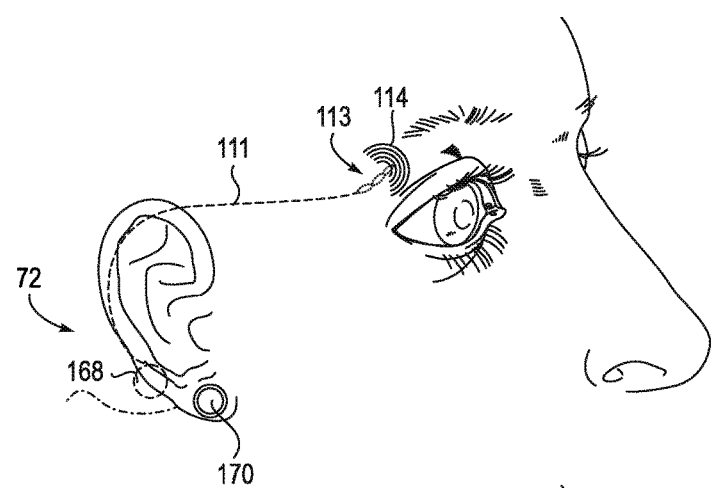
FIG. 6A illustrates a power source and a microstimulator with a stimulation control circuit.

FIG. 6A illustrates a power source and a microstimulator with a stimulation control circuit. The power source may be implemented as battery 170. Battery 170 may or may not include any intelligence and logic. Battery 170 may provide power to microstimulator 168. Microstimulator 168 may receive power from battery 170, generate a signal, and transmit the signal over leads to electrodes 113. Microstimulator may be implanted within the patient, for example within the mastoid region 72 of the temporal bone of the patient. The microstimulator may be positioned subcutaneously just beneath the skin, without removing a portion of bone, or subcutaneous with removing a portion of bone. The portion of bone that may or may not be removed may include the mastoid portion of the temporal bone. The microstimulator may be positioned external to the skin, with the lead percutaneously tunneled through the skin.

Figure 6B:
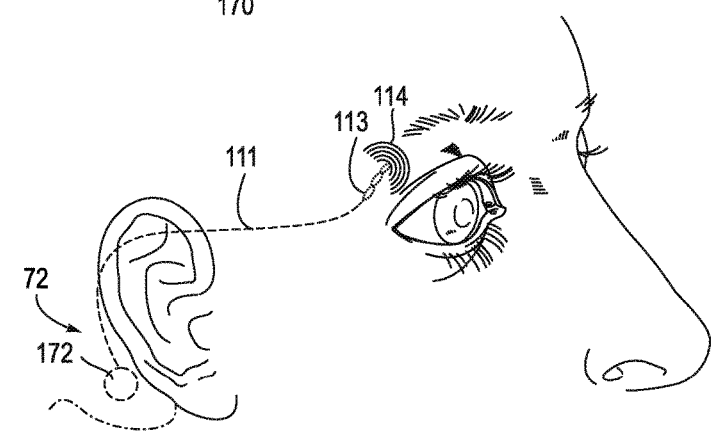
FIG. 6B illustrates a pulse generator implanted into a patient.

FIG. 6B illustrates a pulse generator implanted into a patient. Pulse generator 172 of FIG. 6B may include a power source and be implanted within a mastoid region 72 of the patient's temporal bone. Pulse generator 172 may generate a signal for stimulating anatomical targets and transmit the signal to one or more electrodes 113 over leads 111.

Figure 7:
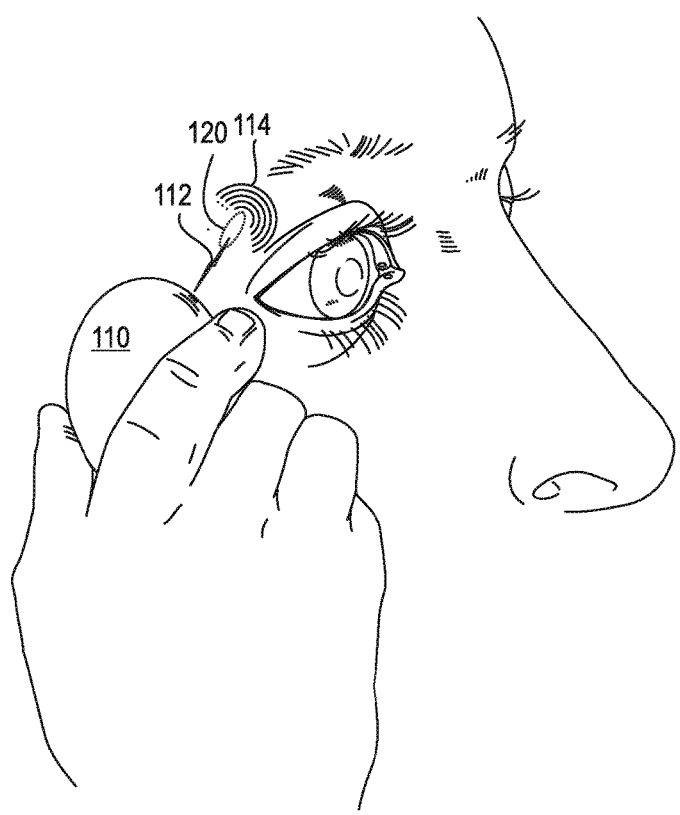
FIG. 7 is another exemplary controller for use with a stimulation system.

FIG. 7 is another exemplary controller for use with a stimulation system. The stimulation system of FIG. 7 includes controller 110 and microstimulator 120 which receives a waveform 112 and outputs a signal 114 for stimulating one or more anatomical targets of a patient, such as a lacrimal gland. Controller 110 may be implemented external to microstimulator 120 and the body of the patient. In various embodiments, the controller 110 of FIG. 7 may be implemented as a hand held device. The hand held controller 110 may be manipulated to indicate when the waveform 112 should be applied to the microstimulator in order to stimulate a lacrimal gland or other anatomical target. The handheld controller may be preset by a health professional or other person in an office or other location so that the controller operates automatically. The handheld controller may also be manually configured by a patient.

Figure 8A:
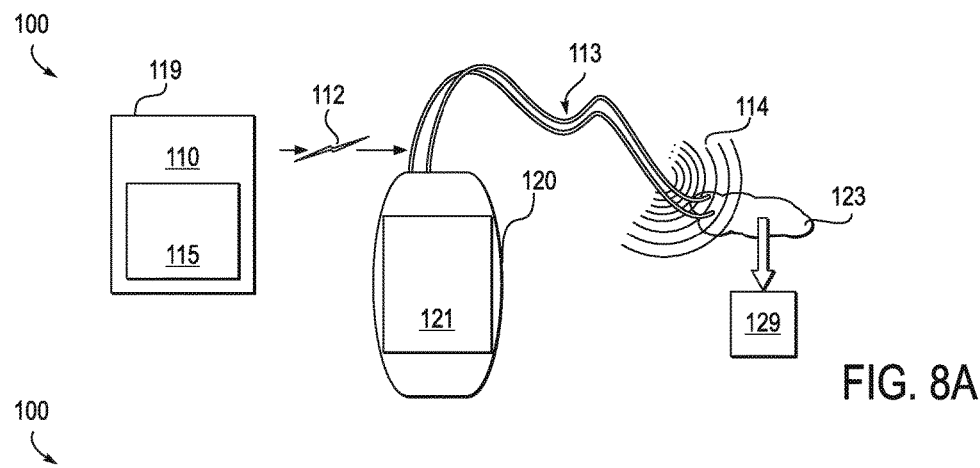
FIG. 8A is a block diagram of a wireless stimulation system.

FIG. 8A is a block diagram of a wireless stimulation system. The wireless stimulation system 100 of FIG. 8A includes a controller 110 and a microstimulator 120. Controller 110 may include a housing 119 and a controller circuit 115. Controller circuit 115 may generate an output signal 112 and transmit the signal to microstimulator 120. The transmitted signal may be a radio frequency magnetic wave and transmitted wireless through air, tissue and other material to microstimulator 120. Controller circuit 115 is discussed in more detail below with respect to FIG. 8C.

Microstimulator 120 includes one or more electrodes 113 and pulse generation circuit 121. The microstimulator 120 may be implanted within a patient and positioned with respect to the controller 110 such as to receive the signal generated by the controller 110. Pulse generation circuit 121 receives the signal generated by controller circuit 115 and generates a pulse from the received signal. The pulse may be DC balanced or other signal and may be applied to an anatomical target 123, such as for example a lacrimal gland. An output signal 114 for stimulating one or more anatomical targets may be applied via one or more electrodes 113 coupled to the pulse generation circuit 121.

When stimulated by the pulse generated by the microstimulator 120, the anatomical target 123 achieves a desired endocrinological outcome 129 such as for example generating tears in a patient. Another example of a desired endocrinological outcome 129 may include, but is not limited to, stimulation of one or more anatomical targets to cause secretion of fluid, electrolytes, and proteins, vasodilatation, increasing the volume of tears, increasing the quality of tears, improving surface health, decreasing tear osmolarity, and decreasing ocular inflammation. In the case of the meibomian glands 128, lipids may be secreted. The microstimulator 120 is discussed in more detail below with respect to FIG. 8C.

Figure 8B:
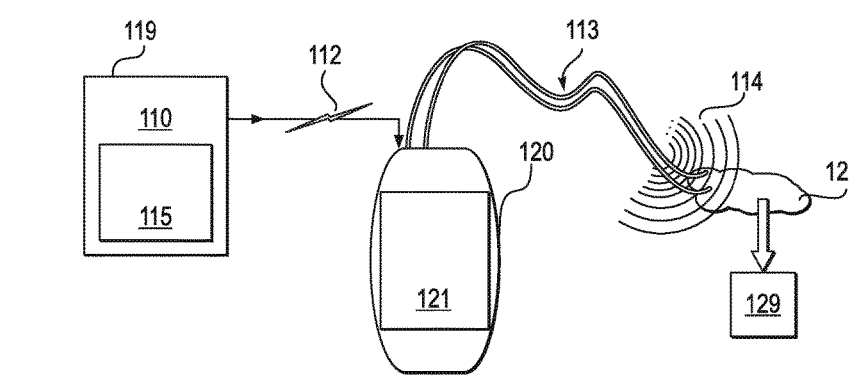
FIG. 8B is a block diagram of a wired stimulation system.

FIG. 8B is a block diagram of a wired stimulation system. The wired stimulation system 100 of FIG. 8B includes a controller 110 and a microstimulator 120. Controller 110 of FIG. 8B may include housing 119 and a controller circuit 115 similar to the controller of FIG. 8A. Controller 110 of FIG. 8B differs from the controller of FIG. 8A in that controller 110 of FIG. 8B transmits an output signal 112 to microstimulator 120 via a wired transmission line, such as a conducting wire or other medium. The conducting wire or other medium may be attached to controller 110 and be routed through a patient's body to microstimulator 120.

Leads 111 between a controller 110 and microstimulator 120 may be tunneled. The tunneling pathway may depend on where the device is implanted. In various embodiments, the tunneling pathway may extend from the ear region (superficial to the temporal bone) to the temporal aspect of the orbit into the superior lateral aspect of the orbit, through the orbital septum and to the anatomical target.

A controller and microstimulator may have configurations in addition to those illustrated in FIGS. 8A-B, including combinations of the configurations illustrated and other configurations. For example, an implantable pulse generator (IPG) may include a controller and a pulse generator as a single device. The IPG may be connected to one or more electrodes via one or more leads. Hence, the IPG implanted within a patient may be deployed in one location within a user and used to stimulate one or more anatomical targets at a different location within the patient, corresponding to the location of one or more electrodes connected to the IPG.

Microstimulator 120 includes pulse generation circuit 121. The microstimulator may be implanted within a patient and may be connected to the wired connection attached to the controller 110. Similar to the circuit 121 of FIG. 8A, pulse generation circuit 121 of FIG. 8B receives the signal generated by controller circuit 115, generates a pulse from the received signal, and applies the pulse to an anatomical target, such as for example a lacrimal gland. When stimulated by the pulse generated by the microstimulator 120, the anatomical target achieves a desired endocrinological outcome 129 such as for example generating tears in a patient.

Figure 8C:
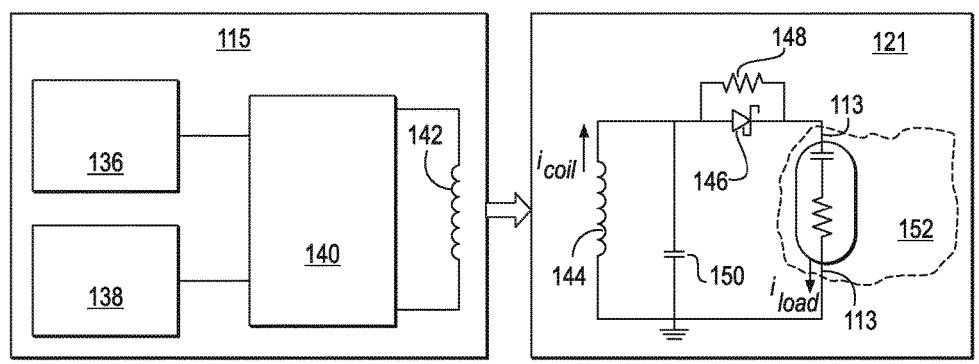
FIG. 8C is an exemplary circuit for implementing a stimulation system.

FIG. 8C is an exemplary circuit for implementing a stimulation system. The circuit of FIG. 8C includes a controller circuit 115 and pulse generation circuit 121. Controller circuit 115 may include a power source 136, input module 138, and controller 140. Power source 136 may provide a voltage source, current source, or other power source to controller 140. The power may be a constant voltage or current or alternating voltage or current. The controller 140 may detect one or more operating parameters of the micro stimulator. Controller circuit 115 of FIG. 8C may be used to implement controller 110 discussed with respect to other figures herein.

Input 138 may provide one or more inputs signals to controller 140. The input signals may be generated from input received from a user such as a patient, a health professional, or other external source. For example, the user input may be a depressed button, an input along a slide bar, or some other input that indicates whether to apply stimulation to one or more anatomical targets such as a lacrimal gland and/or what type of stimulation to apply. The input signals may also be generated from logic inside the input module 138. For example, input module 138 may include logic to apply stimulation to a lacrimal gland periodically, in a ramped fashion, continuously, in a patterned fashion, in response to detecting a condition of low or decreased tear production, or some other condition. In various embodiments the stimulation may be ramped to prevent activation of pain sensation.

Controller 140 may receive power from power source 136 and input signals from input module 138 to generate an output signal. The output signal may be a voltage signal or a current signal applied to controller coil 142, an inductive coil coupled to controller 140. The output signal may vary in frequency, amplitude, period and/or phase based on the input received from input module 138 and power received from controller 140. When the output signal is applied to controller coil 142, the coil 142 may generate a magnetic wave having a radio frequency and amplitude based on the output signal and coil.

Pulse generation circuit 121 may include a microstimulator coil 144, rectifying circuit consisting of diode 146 and/or resistor 148, and a tuning capacitor 150. One end of microstimulator coil 144 (a conductive coil) is connected to a first end of tuning capacitor 150, a first end of resistor 148, and a first end of diode 146. Resistor 148 and diode 146 are connected in parallel, with a first end of the parallel circuit connected to tuning capacitor 150 and microstimulator coil 144 and the second end of the parallel circuit connected to a first electrode 113. The second end of microstimulator coil 144 is connected to the other end of tuning capacitor 150 and a second electrode 113.

The rectifying circuit may implement one or more electrical safety features. Electrical safety features may include one or more elements such as a capacitor in series with the electrodes 113 to limit charge delivery, one or more elements such as a capacitor in series with the electrodes 113 to ensure DC charge balanced stimulation, one or more resistors in parallel with the electrodes 113 and/or series capacitor to allow for DC charge balanced stimulation by capacitive discharge, one or more current limiting diodes in series with the electrodes 113 to limit maximum stimulation current amplitude, one or more zener diodes to limit maximum output voltage. The resistor in parallel with the electrodes may be of a larger impedance than the tissue load impedance to ensure power efficient stimulation. If a resistor is used in parallel with the electrodes 113, resistor 148 may not be used. The current limiting diode may be diode 146. The zener diode may have a turn-on voltage selected to prevent damaging or uncomfortable stimulation amplitudes from occurring The electrodes 113 are connected to one or more anatomical targets, which may include patient tissue 152 such as a lacrimal gland. The tissue 152 may have an impedance which may be described in terms of capacitance and resistance (as illustrated by the capacitor icon and resistor icon within tissue block 152 of FIG. 8C). In various embodiments, pulse generation circuit 121 may be a passive stimulation circuit. The passive stimulation circuit may include a tank circuit. The passive stimulation circuit may include one or more variable resistive elements, variable capacitive elements, variable inductance elements, variable non-linear elements and one or more electrodes. The variable resistive elements, capacitive elements, inductive elements, or non-linear elements may be used to alter a characteristic of the pulse generation circuit 121, such as the resonant frequency, or stimulation parameter such as for example amplitude. The variable resistive elements, capacitive elements, inductive elements, or nonlinear elements may be modified through delivery of energy to the microstimulator 120. Variable resistive elements, capacitive elements, inductive elements, or nonlinear elements may be reversibly varied, or irreversibly varied.

In operation, a magnetic field generated by controller coil 142 is applied to microstimulator coil 144. Microstimulator coil 144 generates a current $i_{coil}$ as a result of the applied magnetic field. The generated current is applied to tuning capacitor 150. When the magnetic field has varying amplitude, the tuning capacitor stores charge. The current applied to the rectifying circuit of resistor 148 and diode 146 produces a pulse at electrode 113 connected to the rectifying circuit. A current $i_{load}$ is generated through the tissue, or anatomical target. The load current travels to the second electrode connected to the other end of the tuning capacitor opposite of the rectifying circuit.

The tuning capacitor may allow for the device to be tuned externally from the microstimulator. The variable capacitor could be adjusted to modify the output of the stimulator. In various embodiments, the microstimulator may include a tuning resistor. Similar to the variable capacitor, the tuning resistor may be adjusted externally from the stimulator to modify the output of the stimulator. The external tuning may be performed by a device that receives user input or is controlled by a controller 110 or controller circuit 115.

In various embodiments, there is no intelligence or logic implemented at the pulse generation circuit 121. The pulse generation circuit 121 may contain a plurality of coils. The plurality of coils may contain a plurality of tuning circuits. Current from the plurality of coils may be summed using rectifiers. The pulse generation circuit 121 may contain a plurality of zener diodes. The pulse generation circuit 121 may contain elements which allow for controller 110 to detect operating parameters of the pulse generation circuit 121. The pulse generation circuit 121 may contain a full-wave rectification circuit. The waveform 112 generated at pulse generation circuit 121, in particular by controller coil 142, determines the frequency and amplitude of the signal applied to tissue 152 by electrodes 113. For example, as a user provides input to adjust the frequency or amplitude of stimulation current, the controller responds by adjusting the amplitude, burst width, or burst frequency of the transmitted waveform 112 accordingly. The frequency and amplitude of the signal applied to tissue 152 by electrodes 113 is not determined by components of the pulse generation circuit. Amplitude of the signal applied to tissue 152 by electrodes 113 may also be adjusted my modifying the frequency of the magnetic field transmitted by controller coil 142.

A microstimulator may take any of several shapes and forms. FIGS. 9A-J illustrate exemplary microstimulators for use with a stimulation system of the present technology. Each of the microstimulators of FIGS. 9A-J may include pulse generation circuit 121.

Figure 9A:
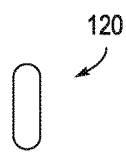
FIG. 9A illustrates a basic microstimulator for use with a stimulation system.

FIG. 9A illustrates a basic microstimulator for use with a stimulation system. The microstimulator 120 of FIG. 9A is shaped like a capsule with a body and two ends. The body may be relatively straight with a cylindrical, square, rectangular, trapezoidal or other shaped cross section and rounded, pointed, or other shaped ends. The basic-capsule shaped microstimulator 120 may include electrodes at one of the curved ends of the device or along the length of the device (electrodes not illustrated in FIG. 9A). The basic microstimulator may include a passive pulse generation circuit for stimulating one or more anatomical targets in a patient and may be hermetically sealed.

The microstimulator 120 may include a coating or covering to assist in implanting the microstimulator 120 in the vicinity of the lacrimal gland. For example, the coating may be an adhesive coating that helps the microstimulator 120 maintain a constant position. In addition to having a coating, the microstimulator 120 may be flexible and conformable. In various embodiments, the coating is bioabsorbable. In various embodiments the coating facilitates encapsulation or stabilization of the microstimulator 120.

Figure 9B:
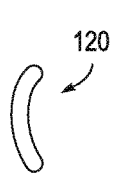
FIG. 9B illustrates a curved basic microstimulator for use with a stimulation system.

FIG. 9B illustrates a curved basic microstimulator for use with a stimulation system. The microstimulator of FIG. 9B may include electrodes and have a body including a cross section and ends shaped similar to the microstimulator of FIG. 9A. Unlike the microstimulator of FIG. 9A, the body of the microstimulator 120 of FIG. 9B may be curved. The curvature of the microstimulator body 120 may be configured to conform to an anatomical structure of a patient, such as a fossa for a lacrimal gland. Implementing a curved basic microstimulator 120 within a patient is discussed in more detail below with respect to FIG. 10B.

Figure 9C:
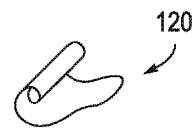
FIG. 9C illustrates a planar pliable microstimulator for use with a stimulation system.

FIG. 9C illustrates a planar pliable microstimulator for use with a stimulation system. The microstimulator 120 may have a first form when it is being inserted into a patient and manipulated to have a second form when it is position in the patient is finalized. For example, the microstimulator of FIG. 9C may be a planar structure which can be unfurled upon implantation through a needle. The microstimulator may unfurl to conform to an anatomical structure of a patient, such as a fossa for a lacrimal gland. Implementing a planar pliable microstimulator 120 within a patient is discussed in more detail below with respect to FIG. 10A.

Figure 9D:
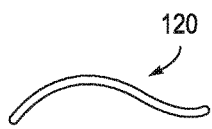
FIG. 9D illustrates another exemplary microstimulator for use with a stimulation system.

FIG. 9D illustrates another exemplary microstimulator for use with a stimulation system. The microstimulator 120 of FIG. 9D is a flexible device shaped to conform to an anatomical structure of a patient, such as a fossa for a lacrimal gland 130 of FIGS. 2A-J. The microstimulator 120 of FIG. 9D includes a first curve in one direction and a second curve in a second direction. In the embodiment illustrated in FIG. 9D, the device curves are formed within a single plane. In various embodiments, the curves may extend in more than one plane.

Figure 9E:
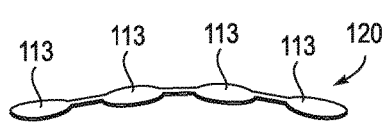
FIG. 9E illustrates a flex segmented microstimulator for use with a stimulation system.

FIG. 9E illustrates a flex segmented microstimulator for use with a stimulation system. The flex segmented microstimulator may include multiple electrodes 113. For example, the microstimulator 120 of FIG. 9E may include four electrodes separated by a body segments. The electrodes may be implemented as part of a pulse generation circuit for stimulating one or more anatomical targets such as a lacrimal gland 10. The electrodes and segments may combine to form a curved shape which may conform to an anatomical structure of a patient, such as a fossa for a lacrimal gland 130 of FIGS. 2A-J. Implementing a flex segmented microstimulator 120 within a patient is discussed in more detail below with respect to FIG. 10C.

Figure 9F:
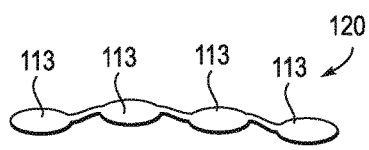
FIG. 9F illustrates a flex conduit segmented microstimulator.

FIG. 9F illustrates a flex conduit segmented microstimulator 120. The flex conduit segmented microstimulator 120 of FIG. 9F is similar to the microstimulator 120 of FIG. 9E in that it has multiple electrodes separated by body segments. Each electrode of the device of FIG. 9F may be implemented as part of a pulse generation circuit such as for example the circuit 121 of FIG. 8C. The conduit segmented microstimulator 120 differs from the device of FIG. 9E in that the overall shape of the device does not form a single curve. Rather, the overall shape of the flex conduit segmented microstimulator 120 of FIG. 9F may be somewhat jagged with each electrode extending about parallel to the other electrodes.

Figure 9G:
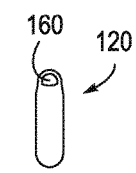
FIG. 9G illustrates a microstimulator having a recapture loop.
Figure 9H:
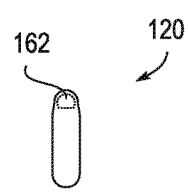
FIG. 9H illustrates a microstimulator having a recapture magnet.

The embodiments of FIGS. 9G-H include features to facilitate minimally invasive retrieval. FIG. 9G illustrates a microstimulator 120 having a recapture loop. The microstimulator of FIG. 9G may include electrodes and have a body including a cross section and ends shaped similar to the microstimulator of FIG. 9A. The microstimulator 120 of FIG. 9G may also include a recapture loop 160. Recapture loop 160 may be positioned at an end of microstimulator 120 as illustrated in FIG. 9G, or along the body of device 120. The recapture loop may be formed by an arm that forms an aperture. The arm may be engaged by an insertion device and/or an extraction device to insert and extract the microstimulator 120 within a patient.

FIG. 9H illustrates a microstimulator 120 having a recapture magnet 162. The microstimulator of FIG. 9H may include electrodes and have a body including a cross section and ends shaped similar to the microstimulator of FIG. 9A, and may also include a recapture magnet 162 implemented in an end (as illustrated in FIG. 9H) or along the body of the device. Recapture magnet 162 may be engaged by an insertion device and/or an extraction device with an oppositely charged metal device to insert and extract the microstimulator 120 within a patient.

Figure 9I:
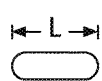
FIG. 9I is a side view of an exemplary microstimulator for use with a stimulation system.
Figure 9J:
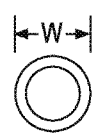
FIG. 9J is a cross section view of a basic microstimulator for use with a stimulation system.

A microstimulator may be used in conjunction with a controller to stimulate an anatomical target such as a lacrimal gland. To stimulate anatomical targets, the microstimulator must be appropriately sized. FIGS. 9I-J illustrate a microstimulator and controller having dimensions suitable for use with an anatomical target such as a lacrimal gland.

FIG. 9I is a side view of an exemplary microstimulator for use with a stimulation system. The microstimulator of FIG. 9I may include electrodes and have a body including a cross section and ends shaped similar to the microstimulator of FIG. 9A. The microstimulator of FIG. 9I may have a length that extends from the outer edge of one end to the outer end of a second end. In various embodiments, the length of the microstimulator may be about 6.0 to 15 millimeters. The width of the microstimulator may be about 1 to 1.5 millimeters. In various embodiments, the length of the microstimulator may be about 10 millimeters. The width of the microstimulator may be about 1.5 millimeters.

FIG. 9J is a cross section view of a basic microstimulator for use with a stimulation system. In various embodiments, the microstimulator may be similar to the device of FIG. 9I and have a width of about 1-1.5 millimeters. In various embodiments, the microstimulator may be similar to the device of FIG. 9I and have a width of about 1.5 millimeters.

A microstimulator may have a length and width selected to permit placement of a portion of the microstimulator or the entire microstimulator adjacent to the lacrimal gland. A microstimulator may also have a length and width selected to permit placement of the microstimulator on, partially in, within or about the lacrimal gland. The microstimulator may be smaller than the lacrimal gland. In various embodiments, the microstimulator is smaller than a portion of lacrimal gland. The microstimulator may be sized to extend the length of the lacrimal gland or fossa for the lacrimal gland. In various embodiments, the microstimulator may be less than the length of the lacrimal gland or fossa for the lacrimal gland.

Figure 9K:
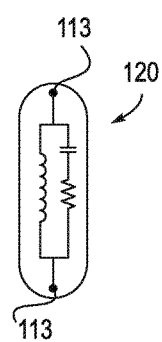
FIG. 9K illustrates a microstimulator with electrodes coupled to pulse generation circuit.

The microstimulator may have different types of leads and electrodes. A microstimulator with different electrodes is illustrated in FIGS. 9K-9Q. FIG. 9K illustrates a microstimulator 120 with electrodes 113 coupled to pulse generation circuit. The pulse generation circuit may have more or fewer components than those illustrated in FIG. 9K. Electrodes 113 may be coupled to the pulse generation circuit at ends of the microstimulator 120.

Figure 9L:
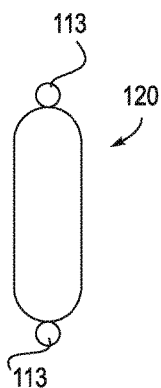
FIG. 9L illustrates a microstimulator having electrodes.
Figure 9M:
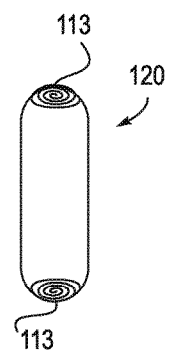
FIG. 9M illustrates a microstimulator having nestled electrodes.

FIG. 9L illustrates a microstimulator having electrodes. The electrodes 113 are attached to microstimulator 120 via small round contact points. The contact points attach electrodes 113 to the exterior of microstimulator 120. FIG. 9M illustrates a microstimulator having nestled electrodes 113.

Electrodes 113 are nestled at the ends of microstimulator 120 and may be configured as a circular pattern. The electrodes may be on both ends of microstimulator 120.

Figure 9N:
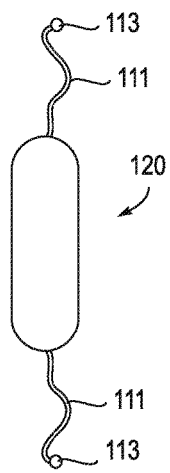
FIG. 9N illustrates another microstimulator having electrodes.
Figure 9O:
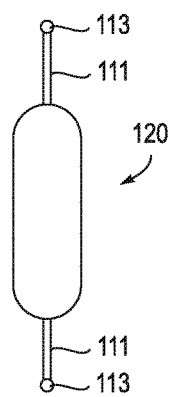
FIG. 9O illustrates another microstimulator connected to electrodes via leads.

FIG. 9N illustrates another microstimulator having electrodes 113. The electrodes 113 of FIG. 9N are attached to a flexible lead 111. Hence, the leads may be curved and manipulated into a different shape. There may be one or more leads. One or more electrodes may be integrated into the body of the device. FIG. 9O illustrates another microstimulator connected to electrodes 113 via leads 111. The leads 111 are rigid and generally maintain a single shape. There may be one or more leads. One or more electrodes may be integrated into the body of the device.

Figure 9P:
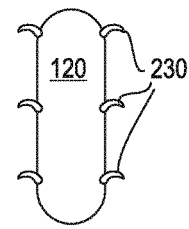
FIG. 9P illustrates a microstimulator having fixation elements.

FIG. 9P illustrates a microstimulator 120 having fixation elements. The fixation elements 230 may include hooks, barbs or anchors and may be configured to maintain a location of the microstimulator while embedded within the patient. In the embodiment of FIG. 9P, the fixation elements 230 are barbs that extend from a length of the microstimulator, extending out therefrom and curving downwards. Though barbs are shown in FIG. 9P, other shapes may be used to implement fixation elements 230.

Figure 9Q:
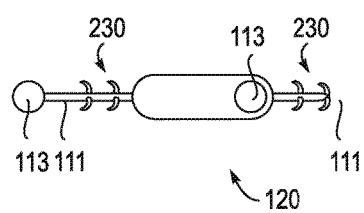
FIG. 9Q illustrates another microstimulator with fixation elements.

FIG. 9Q illustrates another microstimulator 120 with fixation elements. Fixation elements 230 are located on leads 111 between microstimulator 120 and electrodes 113.

Figure 10A:
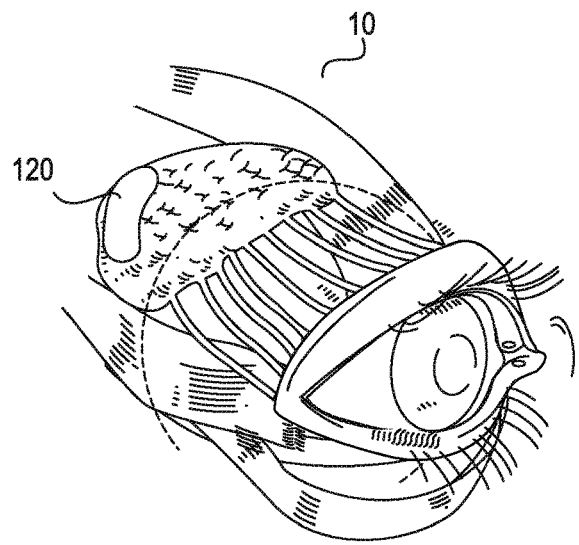
FIG. 10A is a perspective view of a patient's eye with an exemplary microstimulator.
Figure 10B:
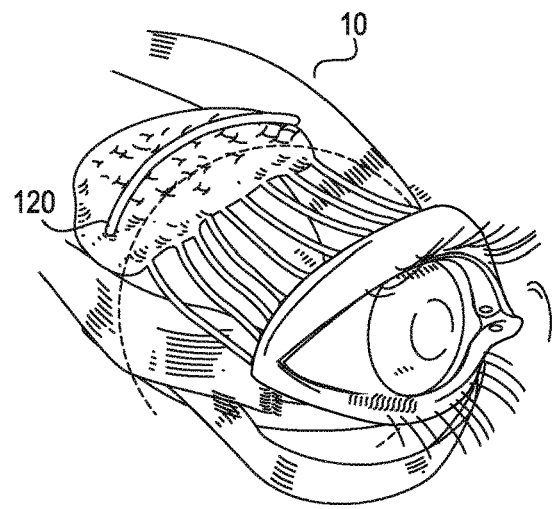
FIG. 10B is a perspective view of a patient's eye with another exemplary microstimulator.
Figure 10C:
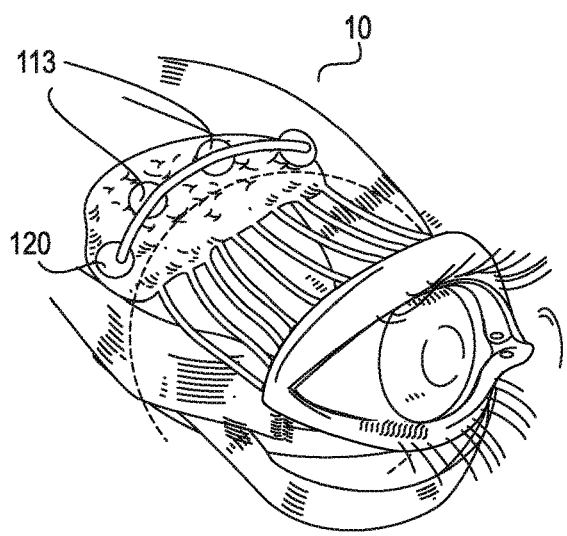
FIG. 10C is another perspective view of a patient's eye with an exemplary microstimulator.

A microstimulator may be positioned on or adjacent an anatomical target such as a lacrimal gland. FIGS. 10A-C illustrate exemplary embodiments of a microstimulator which are positioned on or adjacent a lacrimal gland of a patient.

FIG. 10A is a perspective view of a patient's eye with an exemplary microstimulator. The microstimulator 120 of FIG. 10A is similar to the planar pliable microstimulator discussed above with respect to FIG. 9C. The planar pliable device is positioned on or adjacent to the lacrimal gland and has been unfurled such that a surface of the microstimulator expands over a portion of the surface of the lacrimal gland.

FIG. 10B is a perspective view of a patient's eye with another exemplary microstimulator. The microstimulator 120 of FIG. 10B is similar to the basic curved microstimulator 120 discussed above with respect to FIG. 9B. The basic curved device is positioned on or adjacent the lacrimal gland 10 and curves to conform to an anatomical structure of a patient, such as the fossa for the lacrimal gland 130 of FIGS. 2A-J.

FIG. 10C is another perspective view of a patient's eye with an exemplary microstimulator. The exemplary flex segmented microstimulator 120 of FIG. 10C may include multiple electrodes 113 separated by a body segments. Each of the electrodes may be implemented as part of a pulse generation circuit and may deliver a pulse to stimulate an anatomical target, such as a lacrimal gland 10. In various embodiments, the electrodes and segments may combine to form a curved shape which may conform to an anatomical structure of a patient, such as a fossa for a lacrimal gland 130 of FIGS. 2A-J.

Figure 11:
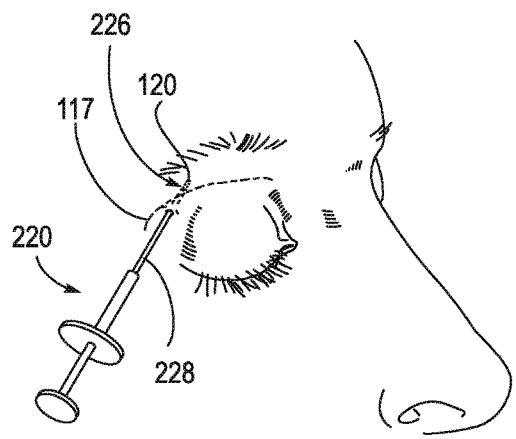
FIG. 11 illustrates an insertion region for deploying a microstimulator.

FIG. 11 illustrates an insertion region for deploying a microstimulator. An insertion device 220 may be used to implant a microstimulator 120 into a patient. The insertion device 220 may insert the microstimulator 120 through an insertion region near the fossa for the lacrimal gland 130 of FIGS. 2A-J. The microstimulator 120 may be secured within the insertion device 220 while being positioned within the patient. Once the insertion device has positioned the microstimulator 120 at the desired location within the patient, the insertion device may deploy the microstimulator 120 in the patient.

Figure 12A:
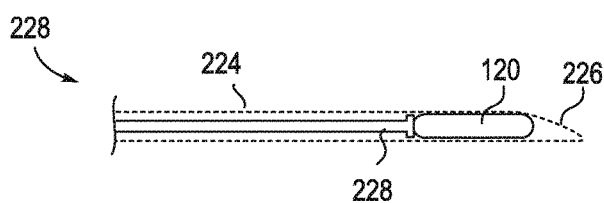
FIG. 12A is a side view of an insertion device for deploying a microstimulator.

FIG. 12A is a side view of an insertion device for deploying a microstimulator. Insertion device 220 includes a housing 224, distal end 226, and device shaft 228. Microstimulator 120 is secured near distal end 226 of insertion device 220. Insertion device 220 may position the microstimulator 120 at or adjacent an anatomical target, such as a lacrimal gland, within a patient while the microstimulator 120 is secured as shown. In various embodiments, the insertion device 220 is a 12 or larger gauge needle. In various embodiments the insertion device 220 contains elements for positioning the insertion device in a location which facilitates safe and accurate delivery of the microstimulator 120. The insertion device may house the microstimulator 120 in a non-needle canula. The insertion device may contain one or more energy storage devices to facilitate insertion, for example a spring. The insertion device may contain an element with which the implanting physician triggers the insertion or deployment of the micro stimulator, such a plunger or button.

Figure 12B:
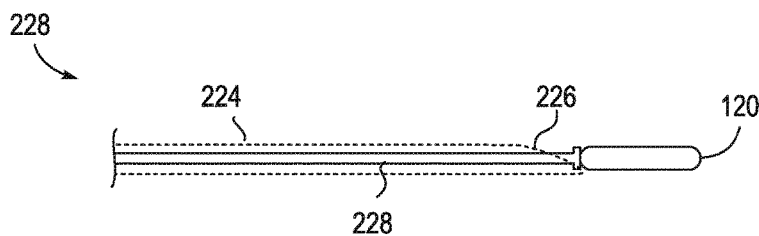
FIG. 12B is another side view of an insertion device for deploying a microstimulator.

FIG. 12B is another side view of an insertion device for deploying a microstimulator. The insertion device of FIG. 12B is similar to that of FIG. 12A, except that the microstimulator 120 is positioned outside the distal end of insertion device 220. The microstimulator 120 may be displaced to a position outside the distal end by extending shaft 228 through device housing 224. When installing a microstimulator 120, the microstimulator 120 may be placed on or adjacent an anatomical target such as a lacrimal gland when the distal end of the insertion device 220 is positioned near the target.

Figure 13:
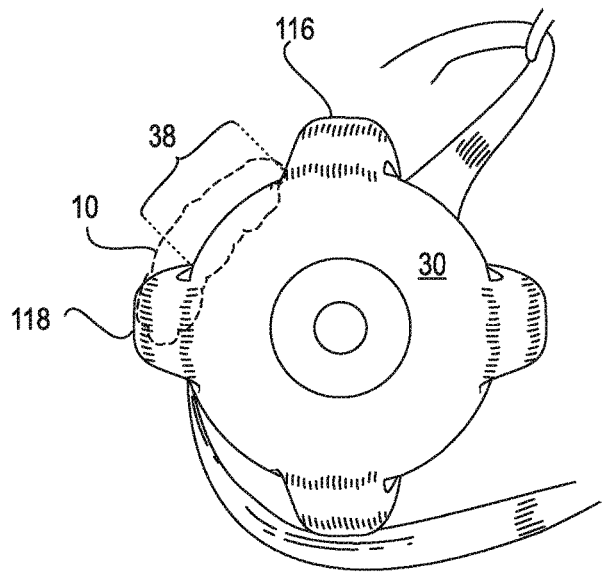
FIG. 13 illustrates an exemplary implant zone for a microstimulator or a multi-electrode lead.

FIG. 13 illustrates an exemplary implant zone for a microstimulator or a multi-electrode lead. Microstimulator 120 or a multi-electrode lead may be positioned within the fossa for the lacrimal gland 130 of the orbit between the superior rectus muscle 116 and the lateral rectus muscle 118. The microstimulator or multi-electrode lead may selectively stimulate an anatomical target such as a lacrimal gland 10 without fully activating the extraocular muscles. For example, stimulation of the lacrimal gland may be sufficient to produce lacrimation or vasodilation of glandular blood vessels without engaging the extraocular muscles that would move the eye in a horizontal or vertical direction.

Figure 14:
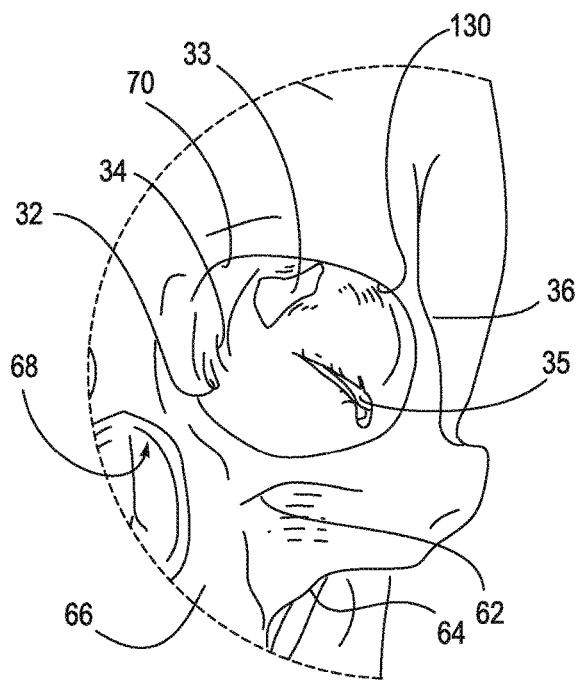
FIG. 14 illustrates another exemplary implant zone for the microstimulator or multi-electrode lead.

FIG. 14 illustrates another exemplary implant zone for the microstimulator or multi-electrode lead. FIG. 14 illustrates the bony structures and regions of the skull that provide access to one or more of the anatomical targets specific to the process of lacrimation. Some of the bony structures and regions include, but are not limited to, the sphenoid bone 36, inferior orbital fissure 35, the infraorbital foramen 62, the maxillary axis 64, the nasal-maxillary area 66, the nasal cavity 68, the fossa for the lacrimal sac 32, the posterior lacrimal crest 34, the inferior medial aspect of the supraorbital process 70, the superior orbital fissure 33 and the fossa for the lacrimal gland 130.

Figure 15:
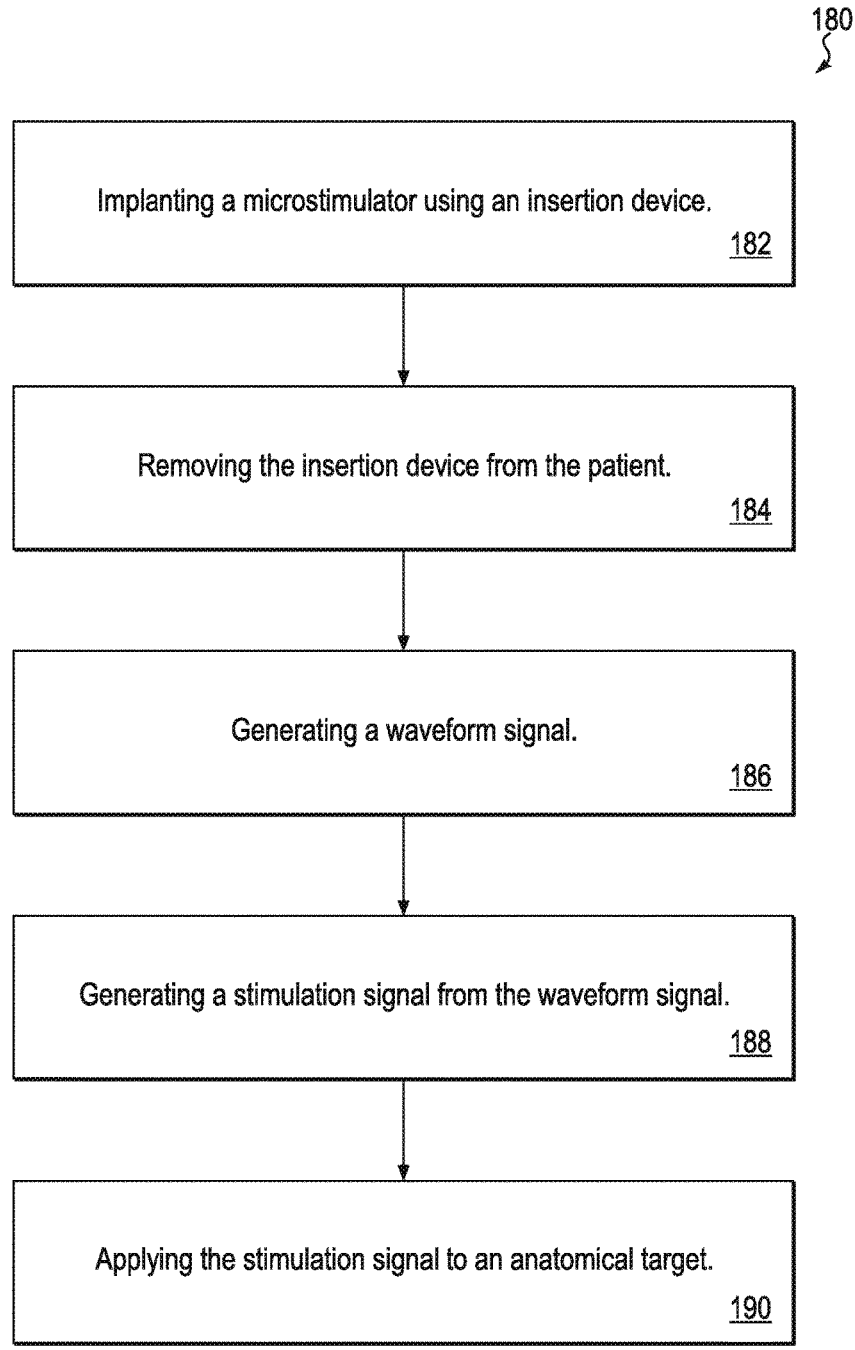
FIG. 15 is a flow chart of a method for stimulating an anatomical target.

FIG. 15 is a flow chart of a method for stimulating an anatomical target. In various embodiments, the method may treat dry eye by stimulating one or more nerves that innervate lacrimal gland tissue. First, a microstimulator may be implanted using an insertion device at step 182. The microstimulator may be implanted about, in proximity to, within or partially in the lacrimal gland. In various embodiments, the microstimulator may implanted into the fossa for the lacrimal gland. Once implanted, the microstimulator may conform to the fossa for the lacrimal gland. The microstimulator may conform to an exterior aspect of a lacrimal gland after implantation. The microstimulator may be implanted using a 12 or larger gauge needle. The insertion device may be removed from the patient at step 184.

A waveform signal may be generated at step 186. The waveform signal may be generated by a controller. The waveform may be generated automatically based on closed loop control or based on user input received by the controller. A stimulation signal may be generated from the waveform signal at step 188. The stimulation signal may be generated by a microstimulator based on the transform generated by the controller and received by the microstimulator. The stimulation signal may then be applied to the anatomical target at step 190. In various embodiments, stimulation may be applied to the lacrimal gland from a microstimulator fully implanted within the orbit of the eye. The stimulation may selectively stimulate one or more nerves that innervate the lacrimal gland. In various embodiments, the stimulation only stimulates one or more nerves that innervate the lacrimal gland.

The stimulation may be electrically selective and may stimulate the one or more nerves that innervate the lacrimal gland without moving the eye in the vertical or horizontal direction. In various embodiments, the stimulation selectively stimulates the one or more nerves that innervate the lacrimal gland without stimulating the ocular muscles discussed with respect to FIGS. 2B and 13. The autonomic efferent fibers may be selectively stimulated over the sensory afferent fibers and the A-delta pain fibers. The efferent fibers may be selectively stimulated over the C pain fibers.

The stimulation may include a current having a pulse amplitude between about 500 µA to about 25 mA. The stimulation may include a pulse amplitude, a pulse width, and a pulse frequency. One or more of the pulse amplitude, pulse width, or pulse frequency may be varied over the treatment period. The stimulation may have a pulse frequency between about 2 Hz to about 200 Hz. The pulse frequency may be between about 30 Hz to about 40 Hz. The stimulation may include a current having a pulse width between about 50 µsec to about 2000 µsec.

Implanting the device may include identifying an insertion point for implantation based upon a feature of the orbit. In various embodiments, the stimulation may be adjusted in response to a measured variable. The stimulation may be delivered in bursts and may include a current having a pulse width between about 500 µsec to about 1000 µsec. A controller may be positioned in proximity to the microstimulator. The stimulation may be delivered in a pattern. The patterned stimulation may be used to ensure the comfort of the patient. The patterned stimulation may be used to efficacy of the stimulation. The stimulation may be delivered periodically at regular or irregular intervals. Stimulation bursts may be delivered periodically at regular or irregular intervals. The stimulation amplitude, pulse width or frequency may be modified during the course of stimulation. For example, the stimulation amplitude may be ramped from a low amplitude to a higher amplitude over a period of time. Stimulation amplitude may be ramped from a high amplitude to a lower amplitude over a period of time. Stimulation pulse width may be ramped from a low pulse width to a higher pulse width over a period of time. Stimulation pulse width may be ramped from a high pulse width to a lower pulse width over a period of time. The ramp period may be between 1 second and 15 minutes. The ramp period may be between 5 seconds and 30 seconds. Stimulation may be delivered at night time. Stimulation may only be delivered at night time. Stimulation may consist of very high frequency pulses to block activity in the target tissue. These very high frequency pulses may be of a frequency between 1,000 Hz and 100,000 Hz.

A magnetic field may be generated by the controller. The magnetic field may be coupled to the microstimulator to generate the stimulation. The magnetic field may be generated in bursts and may have a frequency of about 10 kHz to about 100 MHz or 100 kHz to about 10 MHz.

In various embodiments, the present invention includes a method for treating dry eye by indirectly stimulating one or more nerves that innervate lacrimal gland tissue. First, one or more stimulation electrodes may be positioned adjacent to or in the lacrimal gland. Stimulation may be applied to the lacrimal gland, wherein the one or more electrodes are electrically coupled to a pulse generator. The pulse generator may be implantable in proximity to the one or more stimulation electrodes, to the temporal bone, in the subclavicular pocket, and in a subcutaneous abdominal pocket. A controller may be positioned in proximity to the pulse generator.

Figure 16A:
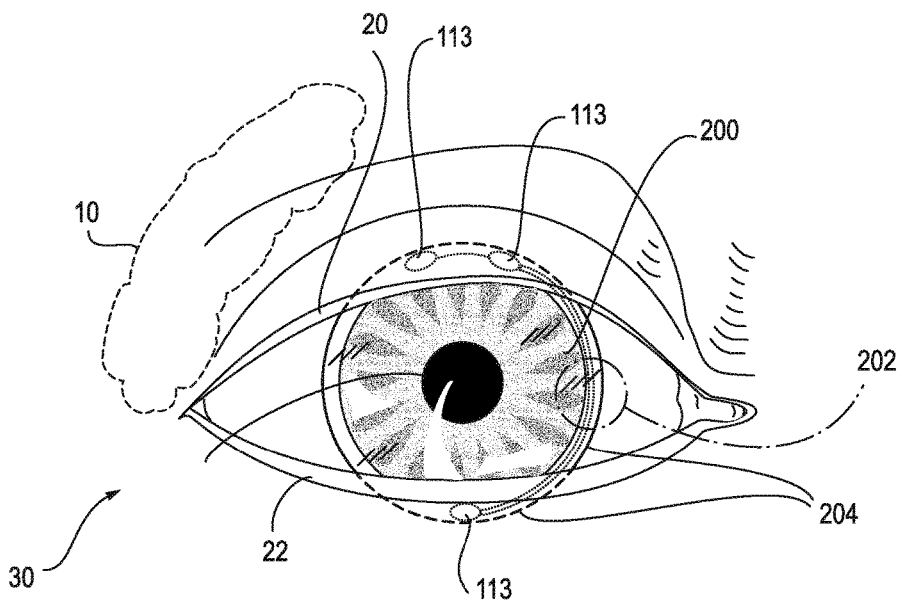
FIG. 16A illustrates a microstimulator implemented with a contact lens.

FIG. 16A illustrates a microstimulator implemented with a contact lens. The embodiment of FIG. 16A includes a contact lens positioned over an iris 200 and having electrodes 113. The contact lens stimulator is in contact with the cornea, and its inner surface conforms to the shape of the cornea and/or the conjunctiva.

Each of one or more electrodes 113 maybe positioned at the outer edge 204 of the contact lens. The device contains two or more electrodes 113 and delivers electrical current to the surface of the eye in order to activate affluent flows. Activation of these fibers results in reflex lacrimation. A patient's upper eyelid 20 and lower eye lid 22 may both close over the contact lens.

Figure 16B:
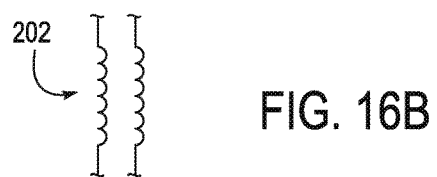
FIG. 16B is an enlarged view of inductive coils for use with the microstimulator of FIG. 16A.

The contact lens stimulator may have a battery/energy storage unit. The stimulator may be powered by a magnet placed within the eyelids. The stimulator may also be powered externally, either continuously or intermittently by an external power source with a coil. The coil may part of an inductive pair of coils 202. FIG. 16B is an enlarged view of inductive coils 202 for use with the microstimulator of FIG. 16A. The power source using inductive coils 202 could be implemented in a handheld device, a pair of sunglasses, or other devices such as those described in FIGS. 3, 5, and 7. The microstimulator may be activated by blinking an eye, in which case a blink detection mechanism would be used in conjunction with the microstimulator.

Figure 17:
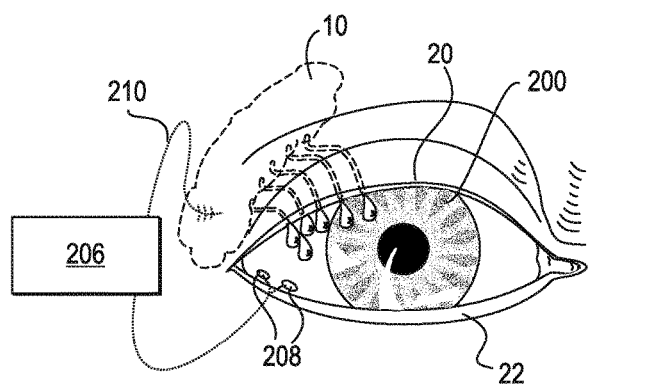
FIG. 17 illustrates a microstimulator implemented with closed loop control of lacrimal stimulation.

FIG. 17 illustrates a microstimulator implemented with closed loop control of lacrimal stimulation. The environment of FIG. 17 includes a lacrimal gland 10, stimulator 206, and an eyeball system. Stimulator 206 may have sensors 208 positioned on the patient's eyeball. The stimulator 206 may be connected to sensors 208 and to stimulator lead 210. Stimulator lead 210 may extend between stimulator 206 and one or more anatomical targets, such as lacrimal gland 10. When stimulated by one or more signals, tears may be produced under upper eye lid 20 and may travel over an iris 200 of the patient's eye assembly.

Closed loop stimulation works by detecting a condition (surface impedance to detect wetness) that provides information about the requirement of tear production and generating a condition signal. The device then modulates its output in response to this condition signal to modify its output in tear production. Detecting the condition may include measurement of one or more variables. Measured variables for use in the closed loop stimulation may include one or more of tear conductivity, tear volume, and gland conductivity. A sensing element may be part of an implantable microstimulator, or could be separate (e.g. a contact lens, part of the controller, etc.) from the implanted microstimulator. The adjustment of stimulation output may be based on an algorithm.

While specific microstimulator implant locations have been illustrated and described above, other implant locations and relative positions between a microstimulator, the lacrimal gland and the surrounding anatomy are possible. Given the variation between patient treatment conditions and human anatomy, numerous alternative microstimulator placements and variable degrees of interaction with the targeted tissue are also considered within the scope of the disclosure. As such, a microstimulator may be positioned such that all or a portion of a microstimulator is adjacent, on, in, or within a target tissue, such as the lacrimal gland. All or a portion of a microstimulator refers to a body, casing or other electrically inactive element or the electrically active elements such as electrodes. Each of these relative positions may be understood in terms of spacing and invasiveness to the lacrimal gland or other target structure. Positioning that is adjacent refers to a placement that is not within direct physical contact but within the stimulation zone of any active element of the microstimulator. Positioning that is on refers to a placement in physical contact with the lacrimal gland or stimulation target. Positioning that is in refers to the insertion by penetration or fixation of at least a portion of the microstimulator. As such, in the lacrimal gland or in a stimulation target would encompass the use of one or more penetrating elements—including electrically active elements like electrodes or electrically passive elements like a hermetically sealed housing, a casing or one or more fixation elements (i.e., a tine, a barb, a hook and the like). In light of the above, within means that the microstimulator is completely within an implant location or position. For example, a microstimulator may be considered within the orbit when it is placed completely within the orbit. Additionally or alternatively, a microstimulator may be considered within the lacrimal gland when it is implanted completely within the gland. For example, a microstimulator may be held within a needle used to inject the microstimulator not only into a position in the orbit but actually within the lacrimal gland itself. Implanting within may be accomplished, for example, using the device and technique described above in FIGS. 12A and 12B.

Still further variations in the placement of a microstimulator are possible in terms of the physical placement of the microstimulator relative to the targeted tissue as well as surrounding structures. Oftentimes it is the case in the field of implanted stimulations systems, optimal placement of a microstimulator adjacent to the targeted structure to achieve the desired modulation or stimulation result is tensioned against unintended damage to or unwanted stimulation of adjacent structures. One specific example would be placement of a microstimulator to achieve enhanced lacrimal gland activity that inadvertently resulted in muscles firing to cause eyelid shuttering or flickering or, in another example, undesired eye movement. Both of these examples illustrate adverse reactions to be avoided during lacrimal stimulation. Embodiments of the present invention may be considered selective to the targeted tissue through the use of one or both of electrical selectivity or physical selectivity. Electrical selectivity includes the adjustment of one or more electrical variables or aspects of the applied neuromodulation signal to control the placement, intensity, neuronal fiber-type recruitment or stimulation zone of the microstimulator. Physical selectivity refers to the placement or position of the microstimulator within the body in proximity to the stimulation target but also considers the adjacent tissue as well. In some cases, a microstimulator is placed so that when the stimulation current is delivered, it will generate electrical fields in the target tissue that are sufficient to induce cellular activity. Alternatively, the electric field in the non-target tissue are insufficient to produce any deleterious effect such as undesired motor response (i.e., eye lid flutter or eye movement as discussed herein).

With reference to FIG. 13, consider the location of the lacrimal gland 38 relative to the rectus muscles of the eye 116, 118. In one illustrative example, a microstimulator may be positioned along the lacrimal gland 10 by in a medial portion of the stimulation zone 38. Such a position would be physically selective to the gland over the adjacent muscles. The stimulation pattern used could also be devised so that the stimulation signal induces activity by the gland with no, low or imperceptive amounts of energy reaching the adjacent muscles. Here, no, low or imperceptive amounts of energy relates to an amount that is below that level resulting in undesired results, such as an undesired motor response. In view of specific treatment or anatomical conditions for a patient, a microstimulator may be positioned in any of a number of different orientations relative to a target implantation site. Moreover, the electrical stimulation patterns may be adjusted according to the resulting placement, proximity to the neural target and stimulation effects to be avoided. Such implant orientations include, for example, on or along a superior aspect of a stimulation or a neuromodulation target, on or along a lateral aspect of a stimulation or a neuromodulation target; on or along a medial aspect of a stimulation or a neuromodulation target; on or along a caudal aspect of a stimulation or a neuromodulation target; or, on or along a dorsal aspect of a stimulation or a neuromodulation target.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method for treating a condition of the eye comprising:
    delivering a stimulus to an anatomical target to produce lacrimation, wherein the stimulus is delivered by an implanted microstimulator, wherein the microstimulator comprises a body and one or more electrodes integrated into the body,
    wherein at least one of an amplitude and a pulse width of the stimulus is ramped over a ramp period, and wherein the stimulus does not activate pain sensation resulting from delivery of the stimulus.

2. The method of claim 1, wherein the microstimulator further comprises a passive stimulation circuit.

3. The method of claim 2, wherein the microstimulator is configured to stimulate the anatomical target via the one or more electrodes in response to a magnetic field.

4. The method of claim 3, further comprising generating the magnetic field with an external controller.

5. The method of claim 4, wherein the magnetic field is adjusted based at least in part on input from the user.

6. The method of claim 1, wherein the microstimulator is pliable.

7. The method of claim 1, wherein the body of the microstimulator has a length of about 6 mm to about 15 mm, and a width of about 1 mm to about 1.5 mm.

8. The method of claim 1, wherein the amplitude of the stimulus is ramped from a low amplitude to a higher amplitude over the ramp period.

9. The method of claim 1, wherein the amplitude of the stimulus is ramped from a high amplitude to a lower amplitude over the ramp period.

10. The method of claim 1, wherein the pulse width of the stimulus is ramped from a low pulse width to a higher pulse width over the ramp period.

11. The method of claim 1, wherein the pulse width of the stimulus is ramped from a high pulse width to a lower pulse width over the ramp period.

12. The method of claim 1, wherein the ramp period is between 1 second and 15 minutes.

13. The method of claim 12, wherein the ramp period is between 5 seconds and 30 seconds.

14. The method of claim 1, wherein the stimulus includes a current having a pulse amplitude between about 500 µA and about 25 mA.

15. The method of claim 1, wherein the stimulus has a pulse frequency between about 2 Hz and about 200 Hz.

16. The method of claim 1, wherein the stimulus has a pulse width between about 50 µs and about 2700 µs.

17. The method of claim 1, wherein the stimulus is delivered to one or more nerves that innervates lacrimal gland tissue.

* * * * *